United States Patent [19]

Slovut et al.

[11] Patent Number: 5,285,793
[45] Date of Patent: Feb. 15, 1994

[54] NONINVASIVE DETECTION OF REJECTION IN HEART TRANSPLANT PATIENTS

[75] Inventors: David P. Slovut, Golden Valley; R. M. Bolman, III; Richard W. Bianco, both of Minneapolis, all of Minn.; John C. Wenstrom, Salida, Colo.

[73] Assignee: Regents of the University of Minnesota, Minneapolis, Minn.

[21] Appl. No.: 886,727

[22] Filed: May 21, 1992

[51] Int. Cl.$^5$ ............................................ A61B 5/0452
[52] U.S. Cl. .................................................. 128/706
[58] Field of Search ............... 128/696, 702, 697, 704, 128/708, 660.03

[56] References Cited

U.S. PATENT DOCUMENTS

| | | | |
|---|---|---|---|
| 4,583,553 | 4/1986 | Shah et al. | 128/708 |
| 4,905,707 | 3/1990 | Davies et al. | 128/702 |
| 4,911,170 | 3/1990 | Thomas, III et al. | 128/660.03 |
| 5,058,597 | 10/1991 | Onoda et al. | 128/708 |
| 5,139,028 | 8/1992 | Steinhaus et al. | 128/697 |

OTHER PUBLICATIONS

"Automatic Extractions of Sinusoidal RR-Intervals from ECG-Signals," by B. M. Tsukerman, et al., A. V. Vishnevskii Surgical Institute of Acadamy of Medical Sciences, Moscow, translated from Meditsinskaya Tekhnika, No. 6, pp. 18–21, Nov.–Dec., 1984.

"Technical Note: An Interval Timer with Computer Interface" by R. McGillivray, et al., Journal of Clinical Engineering, vol. 12, No. 6, Nov.–Dec. 1987.

"Computer Analysis of the Electrocardiogram During Esophageal Pacing Cardiac Stress" by Hossein Jadvar, et al, IEEE Transactions on Biomedical Engineering, vol. 38, No. 11, Nov., 1991.

"Analogue preprocessor for the measurement by a digital computer of R-R intervals and R wave widths" by A. Sandman, et al., pp. 191–200, Medical and Biological Engineering, Mar., 1973.

"Improved ECG R-R Interval Measurement" by A. A. Smerdov et al., All Union Medical Electronics Research and Design Institute, L'vov. Translated from Meditsinskaya Tekhnika, No. 2, pp. 22–24, Mar.–Apr., 1979.

"An Algorithm for Microprocessor-Based QRS Detection" by Omar Escalona, et al. Journal of Clinical Engineering, vol. 11, No. 3, May–Jun. 1986.

"Beat-to-Beat Interval Measurement in the Electrocardiogram," by A. S. M. Koeleman, et al., Medical and Biological Engineering and Computing, No. 23, pp. 213–219, May, 1985.

"ECG Variation with R-R Interval and with Time--Since-Breath in Quiet Subjects" by J. E. Goodfellow, pp. 93–94, 1990 IEEE.

"A 24-Hour ECG Monitoring System for Ambulatory Patient," by M. Grulli, et al, pp. 577–580, 1988 IEEE.

"A Simple Processing of R-R Interval Time Sequences to Detect Atrial Fibrillation Subtypes in Ambulatory Patients," G. P. Duca, et al., pp. 255–258.

"Precision Digital Instrument for Calculation of Heart Rate and R-R Interval" by Kenneth D. Taylor, et al., pp. 255–257, IEEE Transactions on Biomedical Engineering, May, 1975.

(List continued on next page.)

Primary Examiner—William E. Kamm
Assistant Examiner—George Manuel
Attorney, Agent, or Firm—Merchant, Gould, Smith, Edell, Welter & Schmidt

[57] ABSTRACT

A method and apparatus for diagnosing heart rejection is disclosed. Heart rejection is diagnosed based on the pattern of interbeat intervals. The interbeat intervals of the heart are measured shortly after transplant to establish a baseline pattern. The patterns of interbeat intervals from subsequent measurements are compared to the baseline to detect changes from the baseline indicating rejection. The apparatus of the invention measures the interbeat intervals using a Schmidt trigger that detects the upstroke of the QRS and produces a corresponding pulse. The intervals between pulses are timed to produce a series of interbeat interval measurements that are stored and analyzed. Software provides for automated pattern analysis.

18 Claims, 34 Drawing Sheets

Anan, T., Sunagawa, K., Araki, H., and Nakamura, M., "Arrhythmia Analysis by Successive RR Plotting," *Journal of Electrocardiology*, 23(3):243–48 (Jul. (1990).

Babloyantz, A., "Some Remarks on Nonlinear Data Analysis of Physiological Time Series." In Abraham, N. B. (ed): *Measures of Complexity of Chaos*, Plenum Press, New York (1989).

Barbaro, V., Bartolini, P., and Fierli, M., "New Algorithm for the Detection of the ECG Fiducial Point in the Averaging Technique," *Medical & Biological Engineering & Computing*, 29:129–35 (Mar. 1991).

Boone, R., Gross, G. W., and Greco-Hunt, V., "Neutral Networks in Radiologic Diagnosis: I. Introduction and Illustration," *Investigative Radiology*, 25:1012–16 (Sep. 1990).

Brown, R., Bryant, P., and Abarbanel, H. D. I., "Computing the Lyapunov Spectrum of a Dynamical System From an Observed Time Series," *Physical Review A*, 43:2787–2806 (1991) (pp. 2789–2791 enclosed).

Bugarin, A., Barro, S., Ruiz, R., Presedo, J., and Palacios, F., "Syntactic Characterization of QRS Morphology," *Annual Int'l. Conf. of the IEEE Eng. in Medicine & Biology Society*, 13(2):588–89 (1991).

Butler, L. A., "Robust Real-Time R-Wave Detection for Microprocessors," *Annual Int'l. Conf. of the IEEE Eng. in Medicine & Biology Society*, 13(2):594–95 (1991).

Cahill, S. J., and McClure, G., "A Microcomputer-Based Heart-Rate Variability Monitor," *IEEE Trans. Biomedical Engineering*, 30(2):87–92 (Feb. 1983).

Casolo, G., Balli, E., Taddei, T., Amuhasi, Jr. and Gori, C., "Decreased Spontaneous Heart Rate Variability in Congestive Heart Failure," *The American Journal of Cardiology*, 64:1162–67 (Nov. 1989).

Chan, K. H., and Lin, J. C., "Microprocessor-Based Cardiopulmonary Rate Monitor," *Medical & Biological Engineering & Computing*, 25:41–44 (Jan. 1987).

Chialvo, D. R., Gilmour, Jr., R. G., and Jalife, J., "Los Dimensional Chaos in Cardiac Tissue," *Nature* 343:653–57 (Feb. 1990).

CIO-AD16Jr. I/O Board Product Literature, Computer Boards, Inc., Mansfield, Mass., pp. 1–3.

CIO-CTR05 16 Bit Counter/Timer Board Product Literature, Computer Boards, Inc., Mansfield, Mass., p. 27.

Eckman, J. P., Kamphorst, S. I., Ruelle, D., "Recurrence Plots of Dynamical Systems." *Europhys. Lett.*, 4(9):973–977 (1987).

Ewing, D. J., Neilson, J. M. M., and Travis, P., "Irregularities of R–R Interval Cycle Length During 24 Hour ECG Tape Recording," *Scottish Medical Journal*, 29:30–31 (1984).

Farmer, J. D., "Information Dimension and the Probabilistic Structure of Chaos." *Z. Naturforsch*, 37a, 1304–1325 (1982).

Farmer, J. D., Ott, E., Yorke, J. A., "The Dimension of Chaotic Attractors." *Physica.*, 7D, 153–180 (1983).

Fraser, A. M., "Information and Entropy in Strange Attractors," *IEEE Trans. Information Theory*, 35(2):245–62 (Mar. 1989).

Fraser, A. M., and Swinney, H. L., "Independent Coordinates for Strange Attractors from Mutual Information," *Physical Review A*, 33(2):1134–40 (Feb. 1986).

Glass, L., and Mackey, Mc, *From Clocks to Chaos the Rythms of Life*, Princeton University Press, Princeton, N.J., pp. 42–48 (1988).

Gleick, J., *Chaos: Making a New Science*, Penjuin, pp. 262–267 (1987).

Goldberger, A. L., Rigney, D. R., and West, B. J., "Chaose and Fractuals in Human Physiology," *Scientific American*, pp. 43–49 (Feb. 1990).

Goldberger, A. L., and West, B. J., "Applicatoins of Nonlinear Dynamics to Clinical Cardiology," *Annals New York Academy of Sciences*, 504 ( ):195–213 (1987).

Grace, A. A., Newell, S. A., Cary, N. R. B., Scott, J. P., Large, S. R., Wallwork, J., and Schofield, P. M., "Diagnosis of Early Cardiac Transplant Rejection by Fall in Evoked T Wave Amplitude Measured Using an Externalized QT Driven Rate Responsive Pacemaker." PACE 14:1024–1031 (1991).

Gregson, P. H., and McKay, W. P. S., "A Robust QRS-Complex Detector Using an Equivalence Class Characteristics," *Annual Int'l. CXonf. of IEEE Eng. in Medicine & Biology Society*, 13(2):596–97 (1991).

Gulick, Denny, *Encounters with Chaos*, McGraw Hill, Inc. (1992).

Gustafson, D. E., Willsky, A. S., Wang, J., Lancaster, M. C., and Triebwasser, J. H., "ECG/VCG Rhythm Diagnosis Using Statistical Signal Analysis—I. Identification of Persistent Rhythms," *IEEE Trans. Biomedical Engineering*, 25(4):344–52 (Jul. 1978).

Gustafson, D. E., Willsky, A. S., Wang, J., Lancaster, M. C., and Triebwasser, J. H., "ECG/VCG Rhythm (List continued on next page.)

Diagnosis Using Statistical Signal Analysis-II. Identification of Transient Rhythms," *IEEE Trans. Biomedical Engineering*, 25(4):353-61 (Jul. 1978).

Haberl, R., Weber, M., Kemkes, B. M., and Steinbeck, G., "Fourier Transformation of Electrocardiogram for Noninvasive Recognition of Acute Rejection after Orthotopic Heart Transplantation in Man." *Biblthca Cardiol.*, 43:128-132 (Karger, Basel 1988).

Haberl, R., Weber, M., Reihenspurner, M., et al., "Frequency Analysis of the Surface Electrocardiogram for Recognition of Acute Rejection after Orthotopic Cardiac Transplantation in Man." *Circulation*, 76:101-108 (1987).

Heinz, G., Laufer, G., Ohner, T., Gasic, S., and Laczkovics, A., "Analysis of Heart Rate Changes in Cardiac Transplant Recipients Relates to Graft Rejection," *The American Journal of Cardiology*, 66:647-48 (Sep. 1990).

Hwang, S., Nam, S., Lee. J., and Lee, M., "A QRS Pattern Analysis Algorithm by Improved Significant Point Extraction Method," *Annual Int'l. Conf. of the IEE Eng. in Medicine & Biology Society*, 13(2):592-93 (1991).

Kariniemi, V., Rovamo, L., and Pohjavuori, M., "Anslysis of Neonatal Heart Rate Variability by a Microprocessor-Based on-Line System," *Journal of Perinatal Medicine*, 13:233-37 (1985).

Kemkes, B. M., Angermann, C., Jaberl, R., Reichenspurner, H., Klanke, D., Anthuber, M., Cokel, M., "Noninvasive Patient Control After Heart Transplantation." *Biblthca Cardiol.*, 43:119-127 (1988).

Keren, A., Gillis, A. M., Freedman, R. A., Baldwin, J. C., Billingham, M. E., Stinson, E. B., Simson, M. B., Mason, J. W., "Heart Transplant Rejection Monitored by Signal-Averaged Electrocardiography in Patients Receiving Cyclosporine." Circulation, 70 (I)I124-I129 (1984).

Kleiger, R. E., Miller, J. P., Bigger, Jr., J. T., Moss, A. J., et al., "Decreased Heart Rate Variabiity and its Association with Increased Mortality After Acute Myocardial Infarction" *The American Journal of Cardiology*, 59:256-62 (Feb. 1987).

Lee, B., Kweon, H., Kim., T., and Lee, M,, "QRS Recognition Using Synthetic and Nonsyntactic Method," *Annual Int'l. Conf. of the IEEE Eng. in Medicine & Biology Society*, 13(2):590-91 (1991).

Mueller, J. K., Gossard, D., Adams, F. R., Taylor, C. B., Haskell, W. L., Kraemer, H. C., Ahn, D. K., Burnett, K., and DeBusk., R. F., "Assessment of Prescribed Increases in Physical Activity: Application of a New Method for Microprocessor Analysis of Heart Rate," *The American Journal of Cardiology* 57:441-45 (Feb. 1986).

Okada, M., "A Program to Measure Time Intervals Between R. Wave Peaks in Real-Time Mode," *Computer Methods and Programs in Biomedicine*, 20:235-40 (1985).

Pan, J., and Thompkins, W. J., "A Real-Time QRS Detection Algorithm," *IEEE Trans. Biomedical Engineering*, 32(3):230-36 (Mar. 1985).

Pande, V. N., Verma., H. K., and Mukhopadhyay, P., "Bedside ECG Monitor Using a Microprocessor," *Medical & Biological Engineering & Computing*, 23:487-92 (Sep. 1985).

Persson, A., and Solders, G., "R-R Variations, a Test of Automatic Dysfunctions," *Acta Neurol Scand.*, 67:285-93 (1983).

Pinciroli, F., and Tresca, R., "A Microprocessor-based Device for Synthesis of R-R Interval Values During Albulatory Monitoring," *J. Med. Eng. Technol.*, 7(5), pp. 241-251 (1983).

Rapp, P. E., "Chaos in the Neurosciences: Cautionary Tales from the Frontier," draft copy, pp. 1-13 (unpublished).

Ravelli, F., and Antolini, R., "Complex Dynamics Underlying the Human Electrocardiogram." *Biol. Cybern.*, 67:57-65 (1992).

Rosenbloom, M., Laschinger, J.C., Saffitz., J. E., Coxz, J. L., Bolman, R. M., III, Branham, B. H., "Noninvasive Detection of Cardiac Allograft Rejection by Analysis of the Unipolar Peak-to-Peak Amplitude of Intramyocardial Electrograms." Ann. Thorac. Surg., 47:407-411 (1989).

Schreiner, W., Laufer, G., Neumann, M., Lahoda, R., Premauer, W., Merksa, T., Teufelsbauer, H., Rothy, W., Laczkovics, A., and Wolner, E., "A Beat-by-Beat Analysis of Electrocardiograms From Cardiac Transplant Recipients," *Journal of Biomedical Engineering*, 13:313-20 (Jul. 1991).

Semb., B. K. H., Abrahamsen, A. M., Carnard, C. N., "Electrocardiographic Changes During the Unmodified Rejection of Heterotoic Canine Heart Allografts." *Scan. J. Thor. Csrdiovasc. Surg.*, 5:120-124 (1971).

(List continued on next page.)

Sgrigna, V., Villani, M., Iannucci, G. Bella, R., Scibilia, G., Allessandri, N., Marino, B., Sciacca, A., Baciarello, G., "Heart Transplant Rejection Detected by Signal Averaged QRS Analysis: Preliminary Results." *G. Ital. Cardiol.*, 19:1119–1124 (1989).

Shaw, R., "Strange Attractors, Chaotic Behavior, and Information Flow." *Z. Naturforsch*, 36a, 80–112 (1981).

Sibley, R. K. Olivari, M. T., Bolman, R. M. III. Ring, W. S., "Endomyocardial Biopsy in the Cardiac Allogaft Recipient: A Review of 570 Biopsises." *Ann. Surg.*, 203(2):177–187 (1986).

Silber, S., Bajaj, R. K., Krik, K. A., and Pohost, G. M., "Accuracy of Digital Holter Monitoring of Extent and Duration of Ischemic Episodes Compared to Analog Recording," *The American Journal of Cardiology*, 65:383–88 (Feb. 1990).

Skinner, J. E., Goldberger, A. L., Mayer-Kress, G., and Ideker, R. E., "Chaos in the Heart: Implications for Clinical Cardiology," *Biotechnology*, 8:1018–24 (Nov. 1990).

Smolensky, M. H., Bergman, Jr., S. A., Barnard, C. N., Beck, W., and Kraft, I. A., "Functional Independence of Donor and Recipient Cardiac Tissues of Single and Double Heart Transplant Patients Revealed by Chronobiology," *European Journal of Cardiology*, 5/2:119–37 (1977).

Stewart, *Does God Play Dice? The Mathematics of Chaos*, Basal Blackwell, Cambridge, MA, pp. 183–191 (1989).

Suppappola, S., and Sun, Y., "A Comparison of Three QRS Detection Algorithms Using the AHA ECG Database," *Annual Int'l. Conf. of the IEEE Eng. in Medicine & Biology Society*, 13(2):586–87 (1991).

Taylor, K. D., and Mandelberg, M., "Precision Digital Instrument for Calculation of Heart Rate and R-R Interval," *IEEE Trans. Biomedical Engineering*, pp. 225–257 (May 1975).

*Textbook of Advanced Cardiac Life Support*, 2nd Ed., American Heart Association (1990).

Warneke, H. W., Schuler, S., Hans-Joachim, G., Matheis, G., Suthoff, U., Muller, J., Tietze, U., and Hetzer, R., "Noninvasive Monitoring of Cardiac Allograft Rejection by Intramyocardial Electrocardiogram Recordings." Circulation, 74 (III):11172–11176 (1986).

Wheeler, T., and Watkins, P. J., "Cardiac Denervation in Diabetes," *British Medical Journal*, 4:584–86 (Dec. 1973).

Zbilut, J. P. Mayer-Kress, G., and Geist, K., "Dimensional Analysis of Heart Rate Variability in Heart Transplant Recipients," *Mathemetical Biosciences*, 90:49–70 (1988).

Method of Delays

| x<br>RR(n) | y<br>RR(n) |
|---|---|
| 0.68497 | 0.68497 |
| 0.68397 | 0.68397 |
| 0.68497 | 0.68497 |
| 0.68298 | 0.68298 |
| 0.66201 | 0.66201 |
| 0.67000 | 0.67000 |
| 0.66800 | 0.66800 |
| 0.67000 | 0.67000 |
| 0.66800 | 0.66800 |
| ⋮ | ⋮ |
| n | n |

(Delay = 0)

FIG. 4B

| x<br>RR(n) | y<br>RR(n+1) |
|---|---|
| 0.68497 | • |
| 0.68397 | 0.68497 |
| 0.68497 | 0.68397 |
| 0.68298 | 0.68497 |
| 0.66201 | 0.68298 |
| 0.67000 | 0.66201 |
| 0.66800 | 0.67000 |
| 0.67000 | 0.66800 |
| 0.66800 | 0.67000 |
| ⋮ | ⋮ |
| n | n |

(Delay = 1)

FIG. 4C

EKG #23-4
No Rejection

EKG #23-6
Moderate Rejection

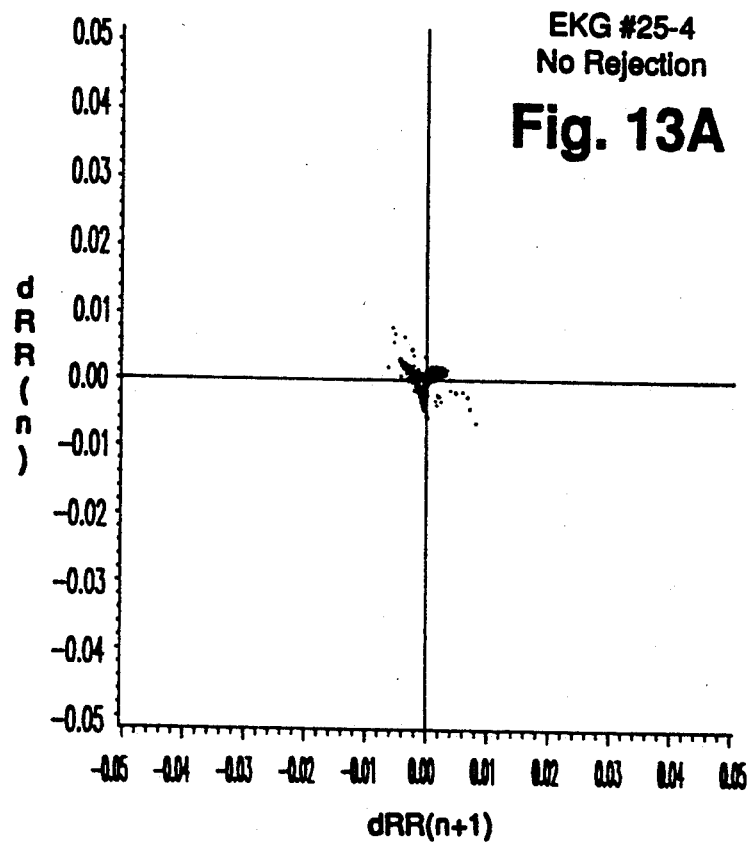
Fig. 13A — EKG #25-4 No Rejection
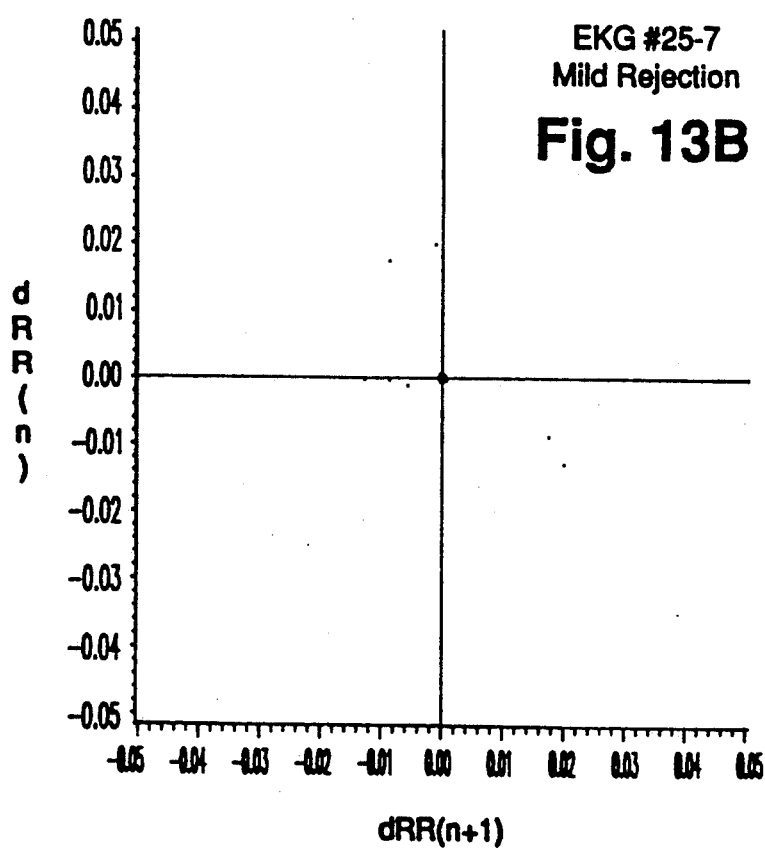
Fig. 13B — EKG #25-7 Mild Rejection

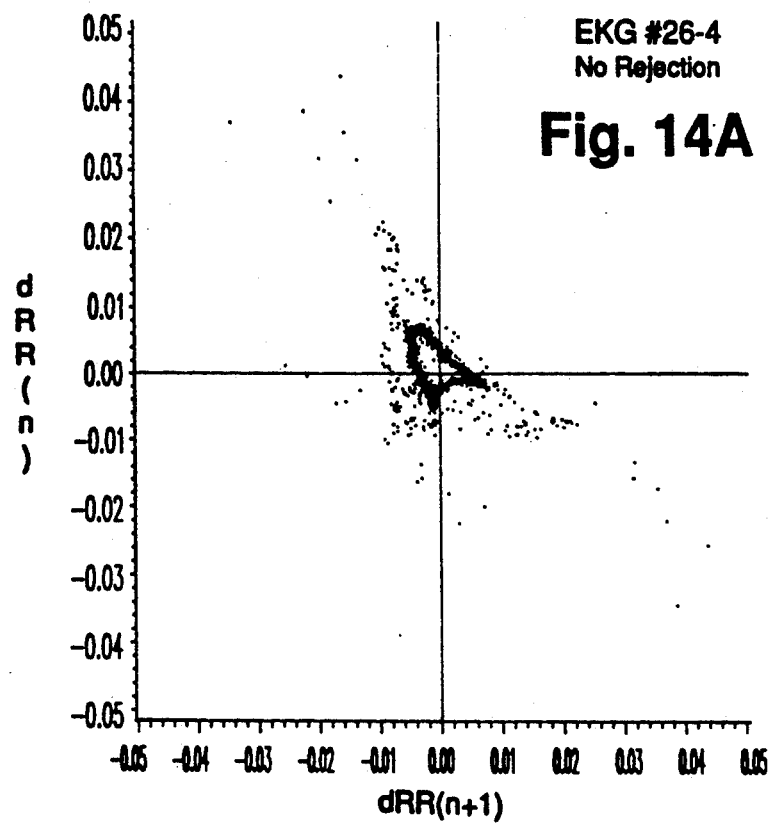
Fig. 14A — EKG #26-4 No Rejection
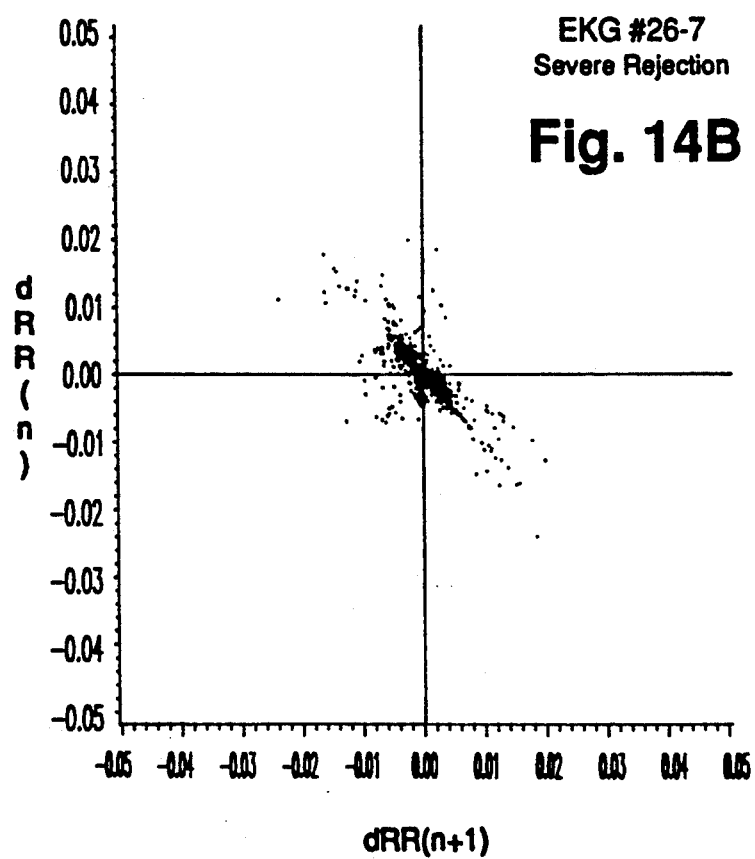
Fig. 14B — EKG #26-7 Severe Rejection

EKG #26-4

"No Rejection"

EKG #26-7

"Severe Rejection"

Mutual Information Canine Heart Transplant Recipients
N = 512 RR Intervals

|  | Mutual Info | Biopsy |
|---|---|---|
| EKG #19 | | |
| day 4 | 0 | No rejection |
| day 6 | 1.10 | mild rejection |
| EKG #20 | | |
| day 3 | 0.09 | No rejection |
| day 12 | 2.46 | Rejection (grade?) |
| EKG #22 | | |
| day 9 | 1.07 | No rejection |
| day 12 | 3.71 | Rejection (grade?) |
| EKG #23 | | |
| day 4 | 0.16 | Inadequate tissue |
| day 6 | 1.06 | Moderate rejection |
| EKG #25 | | |
| day 4 | 1.01 | No rejection |
| day 7 | 2.96 | Mild rejection (1A) |
| EKG #26 | | |
| day 4 | 1.00 | No rejection |
| day 7 | 1.72 | Severe rejection (3B) |

EKG #27 -- excluded for technical reasons

| | | |
|---|---|---|
| EKG #31 | | |
| day 4 | 0.00 | No rejection |
| day 9 | 0.95 | Acute rejection (4) |
| EKG #32 | | |
| day 5 | 0.83 | No rejection (4) |
| day 9 | 1.57 | Acute rejection |

Fig. 17

KRA #1
Severe Rejection

KRA #9
Resolving Rejection

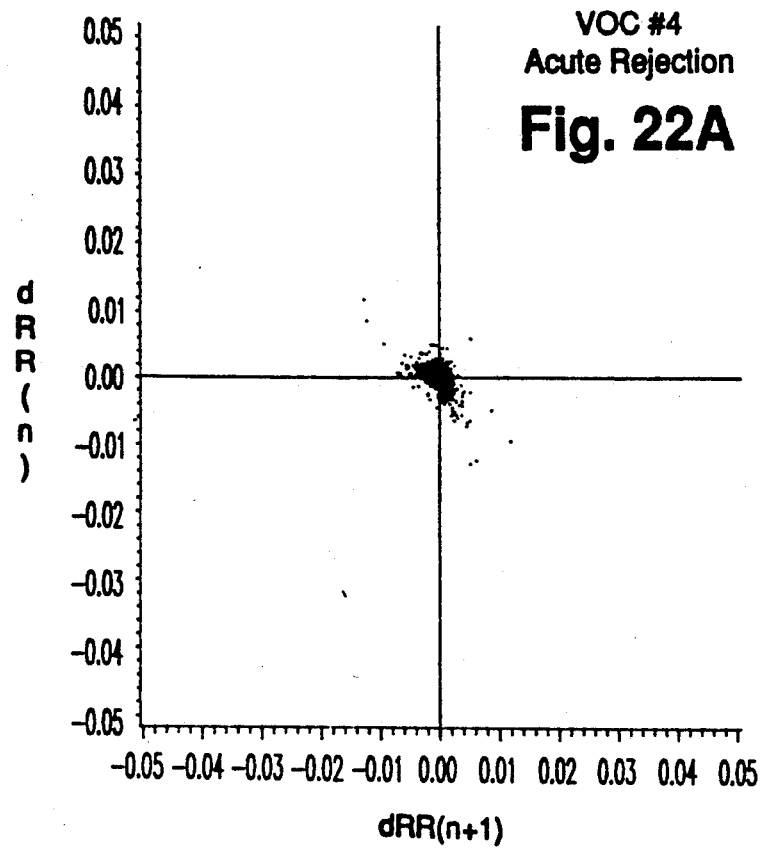
Fig. 22A VOC #4 Acute Rejection
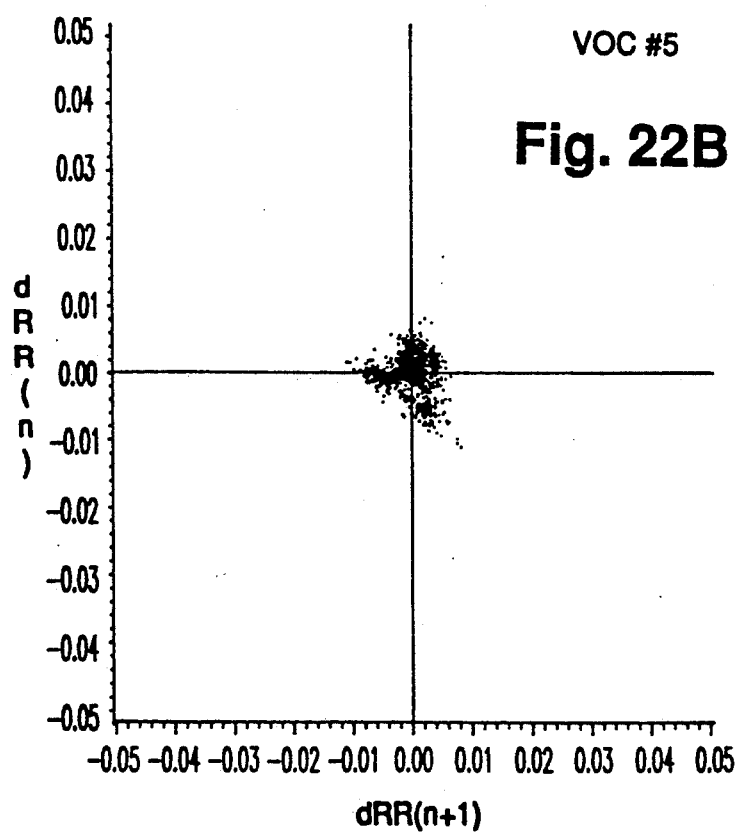
Fig. 22B VOC #5

VOC #9
Acute Rejection

VOC #16
Resolving Rejection

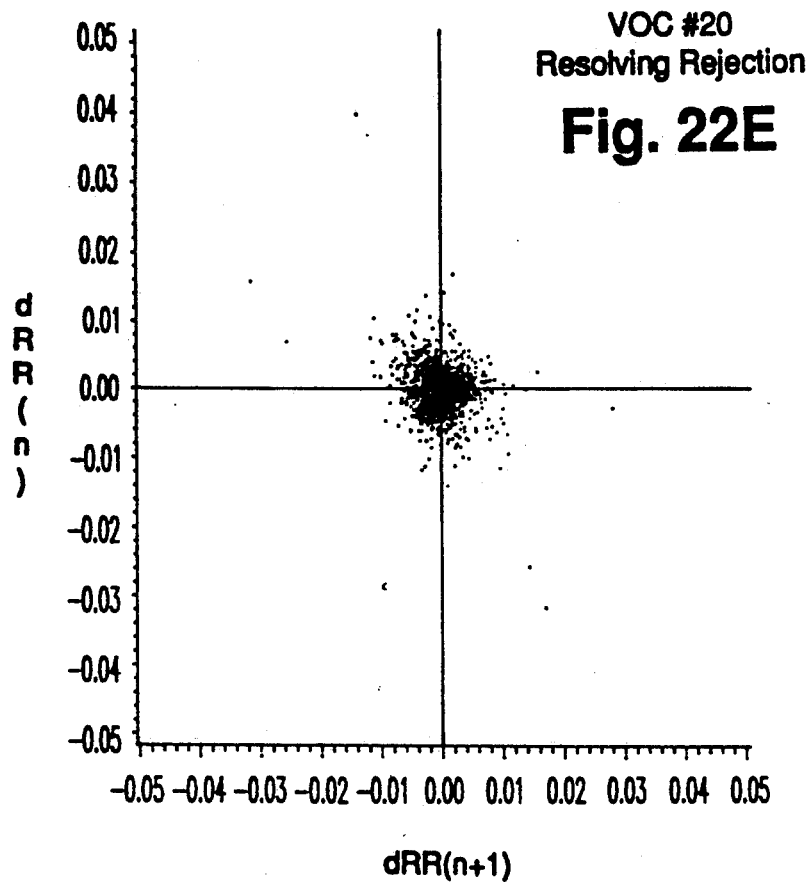
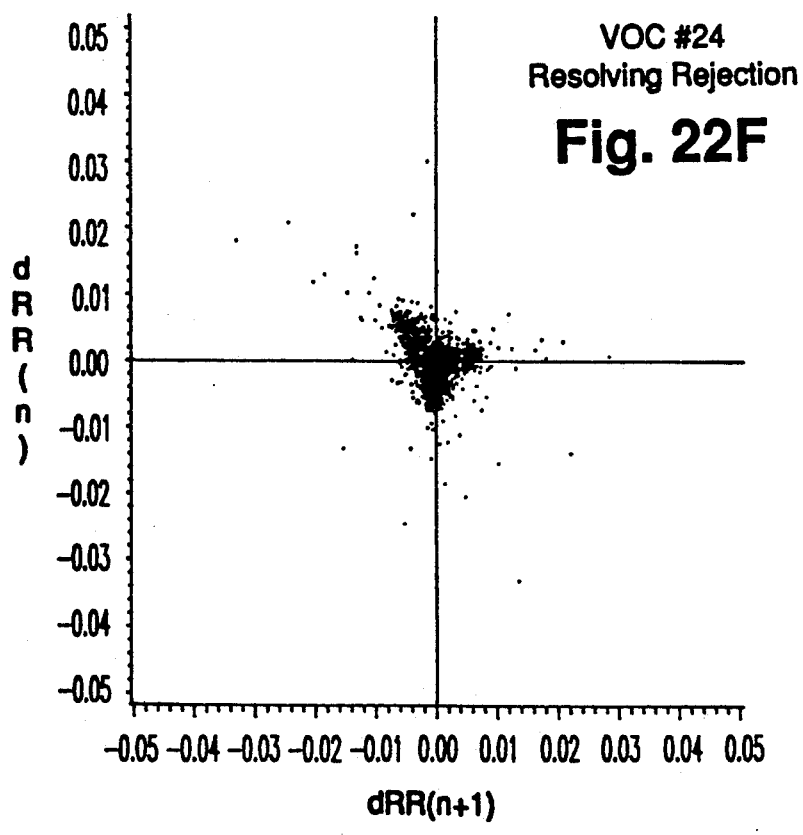

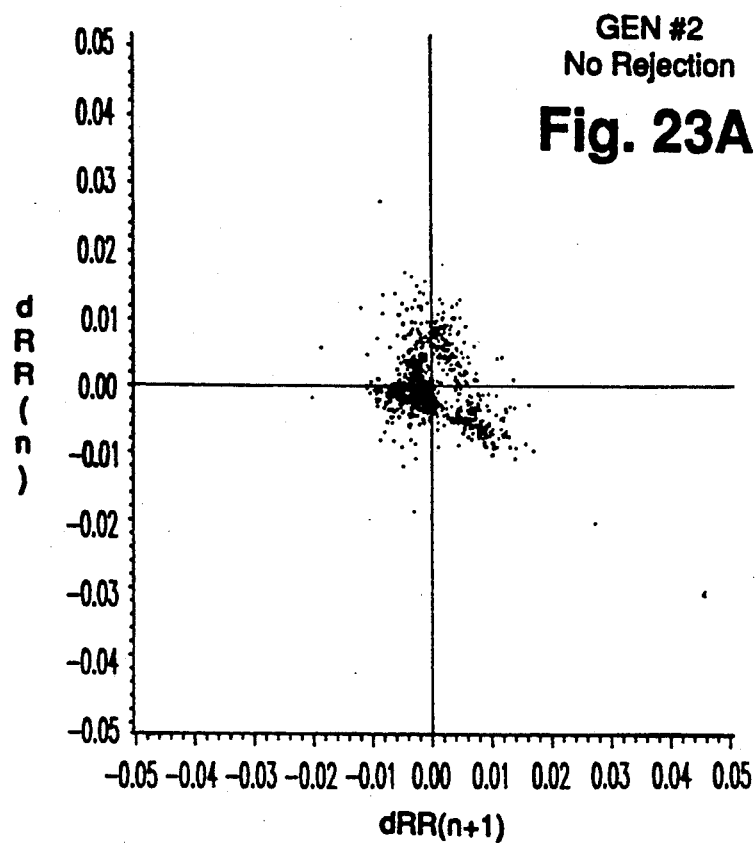
Fig. 23A GEN #2 No Rejection
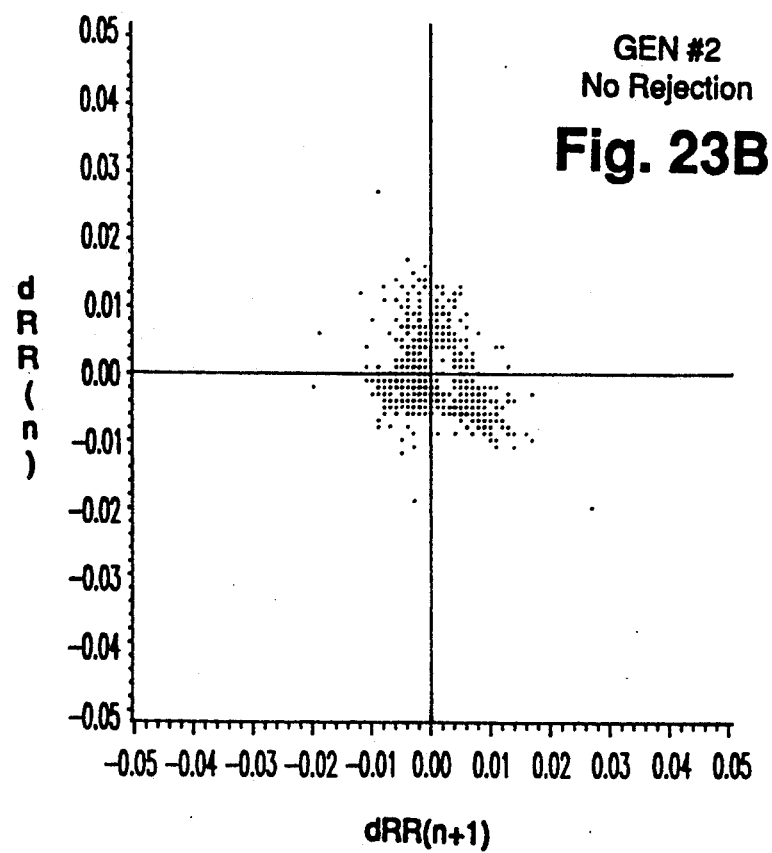
Fig. 23B GEN #2 No Rejection

3-D

2-D

1-D

NONINVASIVE DETECTION OF REJECTION IN HEART TRANSPLANT PATIENTS

TECHNICAL FIELD OF THE INVENTION

The present invention pertains generally to the field of transplant medicine, and more particularly to a device and method for the non-invasive detection of graft rejection in heart transplant recipients.

BACKGROUND OF THE INVENTION

Tissue rejection is the principal cause of heart transplant failures, occurring when a recipient's immune system attacks the transplanted heart. Suppressing this immune system response is critical to the success of heart transplants. Pharmaceutical agents such as Cyclosporine A (CSA), steroids and Azathioprine are used to control and suppress a recipient's immune system response to grafted tissue. However, suppressing a recipient's immune system renders him more vulnerable to infection. Adjusting immune system suppression to the minimum required is thus a major objective. To do this, the transplanted heart tissue must be monitored continuously and carefully for signs of rejection.

Recognizing the onset and severity of rejection is a major problem. Tissue rejection in heart transplant recipients is generally silent until the heart is damaged irreversibly. It is crucial to decide whether or not a patient is rejecting his or her transplanted heart, so that potentially life saving therapy can be started immediately. Thus, early and reliable detection of graft rejection is vital to the success of heart transplants.

At present, the only reliable method for diagnosing rejection requires frequent endomycardial biopsy (EMBx), an expensive (roughly $1,200 or more per procedure), invasive procedure that must be performed by a sub-specialist. The biopsy is studied by a pathologist for the invasion of heart tissue by white blood cells, edema, and dead cardiac muscle cells—the histologic manifestations of rejection. In 85% of cases histologic diagnosis determines treatment for rejection; treatment is determined by clinical judgment in only 15% of cases. Although EMBx is associated with a morbidity of 1-4% in experienced hands, the need for repeated, invasive procedures adds significantly to cost and patient discomfort during post transplant follow-up. A reliable, non-invasive method for detecting rejection is thus needed.

A number of investigators have used a decrease in voltage amplitude on the electrocardiogram (EKG) as a marker for rejection. In the early days of transplantation, a decrease in voltage on the surface EKG correlated well with rejection. With the introduction of CSA in 1982 for immuno-suppression, voltage measurements from surface EKGs became unreliable. More recently, voltage amplitudes from intramyocardial screw-in electrodes have been used to diagnose rejection, as have T-wave amplitudes produced from ventricular pacing. Although these techniques are sensitive and specific for detecting rejection, they require permanent implantation of hardware in the patient's body.

Several investigators have analyzed the EKG using the fast Fourier transform (FFT). FFT measures the spectral power of heart over a range of frequencies. Because the heart rate time series is extremely complicated, frequencies with low statistical weight may be lost because they are indistinguishable from noise. Thus, this approach has not provided a reliable indicator of rejection.

Accordingly, there remains a need for a reliable, non-invasive method for detecting rejection. The present invention provides such a method, and corresponding apparatus, wherein rejection is diagnosed based on the dynamics of heart beat rhythm.

Since the time of Galen, examination of the pulse has been a time-honored ritual in examining a patient. Physicians have learned that dramatic changes in cardiac rhythm may reveal fundamental changes in the health of the heart. The tradition of examining the pulse forms the basis for the novel technique of the present invention for diagnosing rejection in heart transplant recipients. Unlike traditional methods of heart beat analysis based on "gross" variations in heart beat rhythm, the present invention employs the principles of dynamical systems theory to diagnose changes in the health of the heart based on variations which are imperceptible without the use of high precision electronic measurements and computer-aided analysis. These changes from one day to the next may indicate in the heart transplant recipient that rejection has begun.

The present invention uses the investigative tools of dynamical systems analysis to characterize the heart's reaction to rejection. Dynamical systems theory seeks to classify system behavior into one of three classes: 1) steady state; 2) periodic; and 3) chaotic. The theory raises the possibility that seemingly complex unpredictable behavior may be explained by simple deterministic rules. According to P. E. Rapp, in his paper entitled "Chaos in the Neurosciences: Cautionary Tales from the Frontier" (unpublished at the time of filing of this application), the study of chaos in the laboratory is fraught with great difficulty. All measurements contain noise. Differentiating between random noise and deterministic chaos is difficult at best. Worse yet, plausible yet totally spurious results can be obtained from measurements which are largely noise. Therefore, applying the methods of dynamical systems theory to clinical diagnosis remains at the edge of science, and the results of such studies are still viewed with skepticism.

To date, there are a number of publications reporting studies of the dynamics of the heart rhythm, including chaotic dynamics. One general study of heart rate dynamics is reported by Kleiger, et al., in "Decreased Heart Rate Variability and its Association with Increased Mortality after Acute Myocardial Infarction," Am J Cardiol, 59:256-262 (1987) Kleiger et al. report that heart rate variability can be decreased with severe coronary artery disease, congestive heart failure, aging and diabetic neuropathy. Casolo et al. reported similar results for congestive heart failure in the paper entitled "Decreased Spontaneous Heart Rate Variability in Congestive Heart Failure," Am J Cardiol, 64:1162-1167 (1989). Data in these studies were analyzed using only means and standard deviations.

Anan et al. describe a more sophisticated analytical approach in their study "Arrhythmia Analysis by Successive RR Plotting," J. Electrocardiol 23:243-248 (1990). In this paper, the authors looked at the coupling interval-dependent characteristics of arrhythmia based on the gross behavior of heart rhythm, and found that RR interval plotting using data created by the method of delays could be useful both in detecting and in highlighting specific features of various types of arrhythmia, based on the gross behavior of heart rhythm.

Also published in 1990 is a paper by Chialvo et al. entitled "Low dimension chaos in cardiac tissue," Nature, 343:653–657 (1990). This paper reported experimental evidence for chaotic patterns of activation and action potential characteristics in externally driven, non-spontaneously active Purkinje fibers and ventricular muscle. Chialvo et al. did not investigate clinical applications of chaos in cardiac tissue, but restricted their investigation to the action potentials of cells in a petri dish.

A study on the chaotic dynamics of the heart published by Skinner et al. entitled "Chaos in the Heart: Implications for Clinical Radiology," Bio/Technology, 8:1018–1024 (1990), reports that chaos appears to occur in the heart beat time-series. Skinner, et al. discussed in the possible correlation of chaos in heart rhythm with arrythmia, ischemia, myocardial infarction, CHF and old age. In a study of a pig subjected to progressively reduced coronary blood flow, Skinner et al. found that ischemia appeared to produce a decrease in the dimensional complexity of the heart beat as compared to normal.

Another known publication is entitled "Dimensional Analysis of Heart Rate Variability in Heart Transplant Recipients," by Zbilut et al., Mathematical Biosciences 90:49–70 (1988). This paper reports what appears to be a general study of the chaotic dynamics of denervated transplanted hearts. It appears that the primary intent of the study is to test several algorithms for computing dimension on clinical data. The study concludes that there is an apparent reduction of heart rhythm "dimensionality" (a measure of the complexity of a system's behavior in chaos theory) with rejection. However, the paper is inconclusive on this point: "Since we do not claim statistically convincing results at this point, we did not systematically study our dimension estimates for different subsets of our data set" (p. 66). In fact, upon close inspection the clinical results obtained by the study are easily interpreted to suggest that no clear correlation between rejection and reduced dimensionality exists. In particular, based on the study of four transplant patients, Zbilut et al. report that a decrease in the singular-value decomposition estimate of dimension, D-SV, may signal rejection. D-SV for the three non-rejecting patients studied ranges from 2.6–3.6, with standard deviations approaching half of the mean values. However, D-SV for the single episode of rejection equalled 2.9, which falls squarely within their defined "normal" range. Clearly, this result supports the conclusion that there is no clear correlation between a reduction in dimensionality and rejection.

There are several other deficiencies and aspects of the results reported by Zbilut et al. that render their results inconclusive, at least as to the usefulness of dynamical systems theory to diagnose rejection of heart tissue. For instance, there is no indication in the paper as to the level of precision at which the heart beat intervals are measured. Moreover, the phase plots presented in the paper do not appear to differ qualitatively between rejecting and non-rejecting hearts (FIG. 7 vs. FIG. 8), again countering any suggestion that dynamical systems can be correlated with rejection in a transplanted heart. Therefore, the results reported by Zbilut et al. are inconclusive at best, and in fact can be fairly characterized as demonstrating a lack of correlation between rejection and a change in the behavior of heart rhythm.

SUMMARY OF THE INVENTION

By precisely measuring the intervals between heart beats on the order of 100 microsecond precision and better, preparing differential time interval plots of RR interval data created using the method of delays, and correlating with EMBx's for a number of heart transplant recipients in non-rejecting and subsequent rejecting states, the present invention has established a clear, accurate, unambiguous and clinically useful method and apparatus for diagnosing heart rejection based on changes in the dynamics of heart rhythm.

The present invention is based on the discovery that the dynamics of a recipient's heart beat pattern changes significantly during rejection; this change is detectible only if the heart beat intervals are measured with sufficient precision. This change is believed to result from a breakdown in meaningful feedback to the heart's rhythm generator when the heart tissue comes under attack by the recipient's immune system. In a normally functioning denervated transplanted heart, feedback to the rhythm generator produces a continually varying interbeat interval. These variations are on the order of microseconds and milliseconds, and are so small that they are undetectable by standard EKG equipment. Thus, a standard EKG device gives the illusion that the interbeat interval is constant or non-varying, while in fact variability is substantial when higher precision interbeat interval measurements are used.

The present invention uses the interval between R waves (the "RR" interval) to diagnose rejection, but other comparable measures can be used. A series of RR intervals is analyzed using a variety of analytical techniques derived from dynamical systems theory. Examples of these techniques include differential time interval (DTI) plots, recurrence plots, and mutual information analysis.

According to the apparatus of the present invention, there are provided electrodes and a special low noise, high gain preamplifier to acquire the EKG. The analog EKG is digitized and stored, and optionally displayed simultaneously on a monitor and/or rhythm strip recorder. The digitized EKG samples are stored on a computer, preferably a workstation or personal computer, for subsequent analysis. The apparatus further includes a real-time RR interval measurement system, comprising a Schmidt trigger that triggers off of the R wave of the QRS complex, generating a pulse train corresponding the upstroke of the QRS complex. The pulse train is fed to a counter/timer, which times the intervals between heart beats to 4–5 digit precision. These timing results are also stored in an output file. The pulse train is also digitized and stored along with the digitized EKG, referenced to the same time frame. Plotting software allows real-time or off-line plotting of interval variations and patterns, to be used to diagnose heart rejection. The software also identifies changes in the pattern of interbeat intervals from a healthy, normal condition, to one indicating rejection. Based on this analysis, the system produces an indication of the presence or absence of heart rejection to be displayed on the system's monitor or other visual output L device, or on the system's printer. Diagnosis is also accomplished by visual inspection. According to another aspect of the invention, pharmaceutical agents are administered based on the results of the rejection diagnosis.

Thus, the present invention provides an accurate, noninvasive method and apparatus for diagnosing and determining treatment for heart rejection in heart transplant recipients. Because the method and apparatus are noninvasive, easy to operate, relatively inexpensive, and comfortable for the recipient to use, they allow for more frequent patient follow-up and better early detection, monitoring and treatment of graft rejection than the use of EMBX's.

These and further aspects of the present invention are set forth below in the ensuing specification and drawing.

BRIEF DESCRIPTION OF THE DRAWING

FIGS. 4B and 4C are an illustration of creating additional observables using the method of delays according to the present invention;

FIGS. 12A, 12B, 13A, 13B, 14A, and 14B show DTI plots for canine patients with and without rejection;

FIG. 17 is a table showing the results of the calculation of mutual information for a group of canine patients;

FIGS. 22A, 22B, 22C, 22D, 22E and 22F are DTI plots for another human patient VOC, showing several episodes of rejection and treatment;

FIGS. 23A and 23B illustrate the effect of sampling rate on the resolution of DTI plots;

DETAILED DESCRIPTION OF THE INVENTION

In the following detailed description of the preferred embodiments, reference is made to the accompanying drawings which form a part hereof, and in which is shown by way of illustration, specific embodiments in which the invention may be practiced. It is to be understood that other embodiments may be utilized and structural changes may be made without departing from the scope of the present invention.

As outlined above in the Summary of the Invention, the present invention diagnoses heart rejection by analysis of the dynamics of heart beat patterns, and in particular, by comparing the pattern in interbeat intervals against a baseline or reference pattern associated with non-rejection. As described herein, the invention utilizes the interval between R waves (the "RR" interval) to measure the cardiac cycle length. However, the interval between P-waves or other identifiable heart beat events also can be used. As suggested by Zbilut et al., P-waves may be a preferable marker of heart beat intervals, but this suggestion has not been investigated in the present invention.

Figure 1:
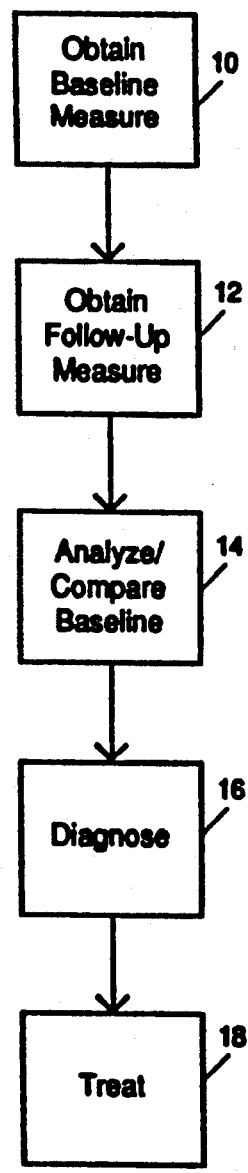
FIG. 1 is a flow chart of an overview of one heart rejection diagnostic method according to the present invention.

FIG. 1 is an overview of the method of diagnosis of the present invention according to one embodiment thereof. The first step 10 obtains baseline, reference measurements from a transplanted heart before measurable tissue rejection can develop, such as three days after surgery. Because each heart may possess a unique rhythm generator, and thus produces a unique pattern of heart beats, each patient preferably serves as his or her own control for future reference. The interbeat intervals for a substantial number of consecutive heart beats are used to establish a norm against which follow up measurements can be compared.

The second step 12 obtains a follow-up measurement of interbeat intervals at some later point in time. Immediately after the transplant, these measurements might be taken every day. Later, measurements might be taken twice a week, then once a week, and then once a month, as needed. In the first year after transplant, patients typically visit clinic for follow-up care and monitoring 30–40 times. Ideally, a patient would have interbeat intervals recorded during each visit to the clinic.

The third step 14 analyzes the follow-up measurement for indications of rejection. This preferably but not necessarily involves comparing the follow-up measurement with the baseline measurement. The fourth step 16 diagnoses the presence or absence of rejection. Finally, the fifth step 18 treats rejection or adjusts rejection medications or therapies based on the diagnosis made in the fourth step 16. Such adjustments may be the administration of greater or lesser doses of pharmaceutical agents used to control rejection. These steps will now be described in more detail.

Figure 2A:
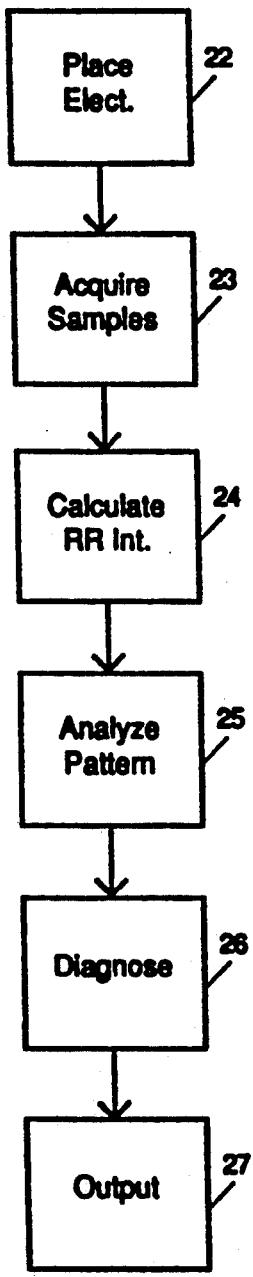
FIG. 2A is a flow chart of one method for obtaining EKG samples and analyzing the interbeat pattern according to the present invention.

FIG. 2A shows the method for obtaining interval measurements. In first step 22 the patient's skin is prepared with 200 grade fine sandpaper and cleansed with an alcohol swab to minimize skin impedance. Self-adhesive Ag/AgCl electrodes are applied to the skin. Electrodes are placed on the recipient's chest to capture R waves of the greatest amplitude. Any lead configuration (I, II, III, etc.) may be used, as the difference between RR intervals remains virtually constant across leads.

Figure 2B:
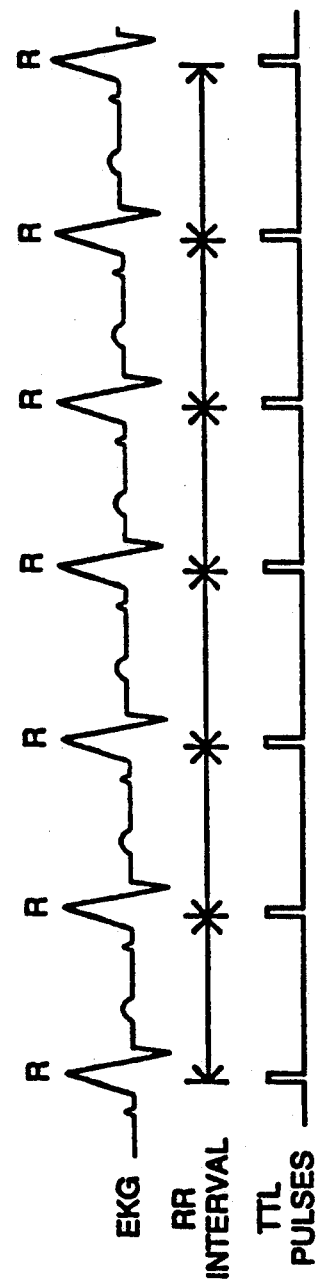
FIG. 2B illustrates a sample EKG and corresponding pulse train according to the present invention.

The second step 23 acquires samples of the patient's EKG an example of which is shown in FIG. 2B. EKGs are amplified with a low-noise, high-gain preamplifier. The EKG is preferably digitized and recorded at 250 samples per second (250 Hz). The samples are stored on a computer for analysis. A workstation or personal computer can be used for this purpose. The recorded EKG can also be displayed simultaneously in real-time on a system monitor, output to a rhythm strip recorder, or both.

Step three (24) measures the RR intervals (illustrated in FIG. 2B) in real-time simultaneously with step two (23) using a Schmidt trigger set to trigger and produce a pulse on the upstroke of R wave of the QRS complex, and a digital counter/timer which times the interval between pulses, or in other words beats, to 4-5 decimal precision (10-100 microsecond precision). The counter/timer outputs a series of interbeat interval measurements (shown in FIG. 2B) which can be stored in an RR output file for later analysis, or plotted in real-time on the system monitor using methods to be described below. The exact number of intervals recorded by the invention is not critical, but in the examples given herein below, a series of approximately 1200 RR intervals were used for the purpose of analysis and diagnosis. It may be desirable to use even more interval measurements for greater reliability and accuracy of analysis.

Figure 3:
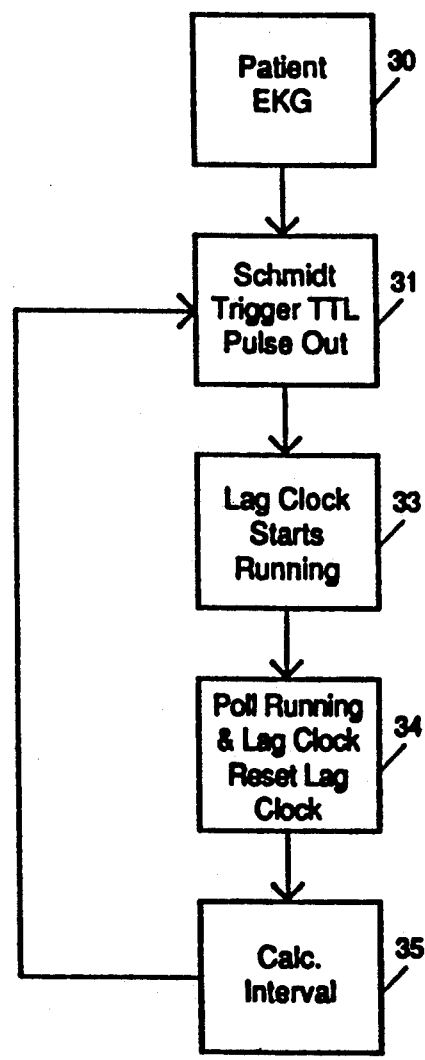
FIG. 3 is a flow chart of the RR interval measurement method according to the present invention.

The method for obtaining RR intervals using the Schmidt trigger and counter/timer is shown in FIG. 3. The analog EKG (30) is fed to the Schmidt trigger (31), which in turn produces a pulse when it detects the upstroke of the QRS complex. The counter/timer includes a continuously running clock and a lag clock. The lag clock starts running when it receives a pulse (33). The running clock and lag clock are periodically polled at a rate exceeding that of the RR intervals (34), and the time of occurrence of the last TTL pulse is calculated by subtracting the lag clock time from the running clock time (at the time when each is polled). The preceding RR interval can then be calculated using the time of the last two TTL pulses (35). The lag clock is reset after it is read. Thus, a series of RR interval measurements are output in real-time to be stored in an output file or used to generate real-time displays of RR interval patterns.

The pulse train produced by the Schmidt trigger in response to the heart beat is preferably digitized and stored along with the digitized EKG using the same timing frame of reference. This allows for an off-line comparison of the pulse train and the EKG to verify the integrity of the pulses and remove any spurious pulses from the RR interval data set.

It is important that the time delay between intervals be measured with great precision. When the EKG is measured at a low ($<1$ KHz) sampling rate, the heart rate of transplant recipients appears virtually constant. At higher, more precise sampling rates, subtle but significant changes in heart rate become evident. As will be demonstrated below with respect to FIGS. 23A and 23B, only by sampling at relatively high rates can the complexity of the heart rate pattern be discerned sufficiently to distinguish rejection and non-rejection.

In the alternative to using the Schmidt trigger and counter/timer, the EKG may be digitized and recorded at a high sampling rate, e.g. $>10$ KHz, and the R wave peaks detected using software analysis, for example, a peak-valley capture algorithm. After the R wave peaks have been marked, the time difference in microseconds between peaks can be calculated, with the results deposited in an output file.

However, this alternative method suffers from two drawbacks. First, digitizing the EKG at high sampling rates results in generation of tremendous amounts of data. At 10 KHz, one megabyte of data is generated for each minute of the recording. Thus, in 30 minutes, our standard recording time at present, more than 30 million characters of data are produced. In addition to storage overhead, such large data files require vast amounts of computer time to process. Performing a peak/valley capture on a 30 megabyte file typically requires one hour. This method makes it difficult to arrive rapidly at a diagnosis. Second, R wave morphology often varies from one peak to the next. In many instances, this can give the impression that the RR interval has changed, when in fact one is merely measuring the effects of a change in morphology. It appears that interval measurements based on R wave upstroke as the fiducial point are more reliable.

Figure 4A:
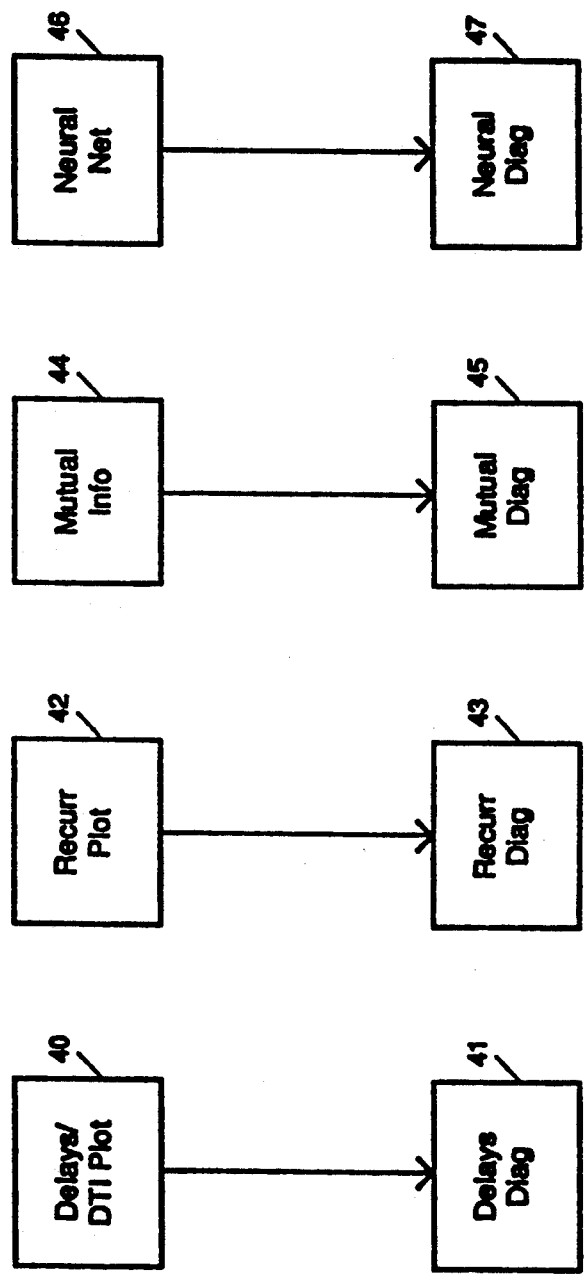
FIG. 4A is a block diagram flow chart showing several methods of analyzing heart beat patterns and diagnosing rejection according to the present invention.

Step five (FIG. 2A, reference number 25) analyzes the RR interval variation. Several methods are known to be effective, and each will be described in detail below. An overview of these techniques is shown in FIG. 4A. The method of delays technique for creating additional observables from the original time series of RR intervals is the precursor to several of these techniques. Using the method of delays the series of RR intervals serves as the x variable. The y variable is created by duplicating the x variable. The "delay" is created by shifting the entire y column relative to the x column. When the delay equals zero, the two columns are aligned. This is illustrated in FIG. 4B for a sample series of "n" RR interval data. When the delay equals one (FIG. 4C), the entire y column is shifted down one row (with respect to the x column). Thus, the second value for x is paired with the first value for y. For a delay of 50, the 50th value for x is paired with the first value of y. Additional variables can be created by making additional duplicates of the x variable.

As will be described in more detail below, the present invention uses several techniques to plot and analyze data sets created by the method of delays, and in particular techniques of nonlinear dynamical systems analysis. Such techniques include Differential Time Interval (DTI) plots 40 in two or more dimensions, recurrence plots 42 and mutual information analysis 44. A neural network method 46 is also possible. No matter which analysis is used, the essence of the analysis step is to detect abnormal variations in the pattern of intervals between successive heart beats.

As previously described in the Summary of the Invention, the present invention is based on the discovery that a heart transplant recipient's RR interval pattern changes significantly during rejection DTI plots, recurrence plots and neural network and mutual information analysis are all ways of detecting the presence or absence of normal or abnormal patterns.

The sixth step (26) (FIG. 2A) provides a diagnosis based on the presence or absence of normal or abnormal patterns.

Step seven (27) outputs the results to a printer, monitor, or other suitable output device. Preferably, the diagnosis is achieved from one or more objective criteria that are susceptible of automation (e.g. neural networks). Alternatively, the diagnosis can be achieved by human visual inspection of one or more plots and/or mutual information results. If the diagnosis is automatically determined, it is displayed on an output device such as a CRT or panel light indicator, output to a printer, or transmitted to another computer by telecommunication.

Figure 5:
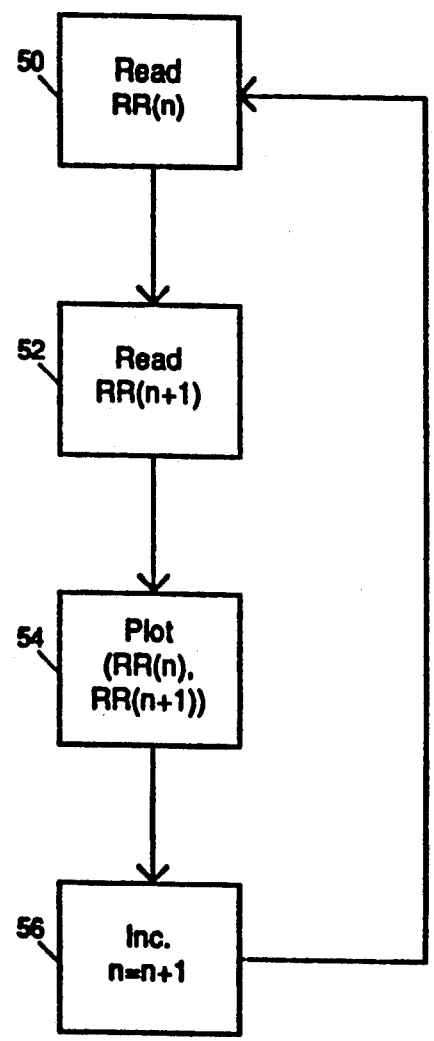
FIG. 5 is a flow chart illustrating the method of delays plotting technique according to the present invention.
Figure 6A:
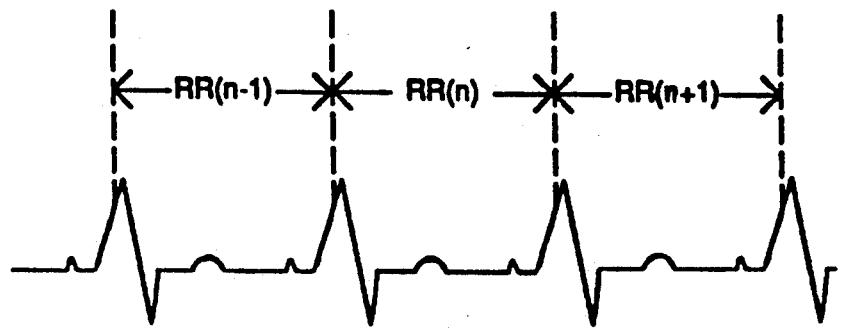
FIG. 6A is an illustration of calculation of differential time intervals according to the present invention.
Figure 6B:
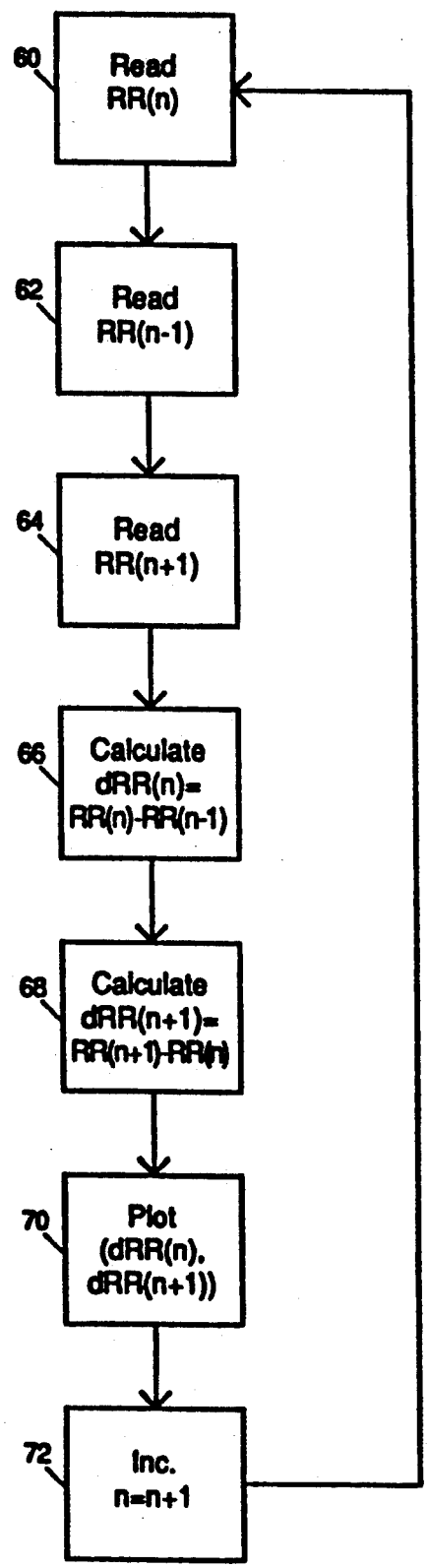
FIG. 6B is a flow chart of the Differential Time Interval (DTI) plotting technique according to the present invention.

FIGS. 5, 6A and 6B illustrate successive RR interval and DTI plotting, respectively. In successive RR interval graphs, the present RR interval is plotted as a function of the succeeding RR interval. The method of this particular type of plotting is shown in FIG. 5. A first RR interval, RR(n), is read (50) from the RR interval output file. The next interval, RR(n+1), is also read (52). The pair of points making up the x-y coordinate (RR(n),RR(n+1)) is plotted (54) on an x-y coordinate plane. The variable n is incremented, and the process repeated until all pairs are plotted. An example of this type of plot is shown in Anan et. al., mentioned above.

Figure 18:
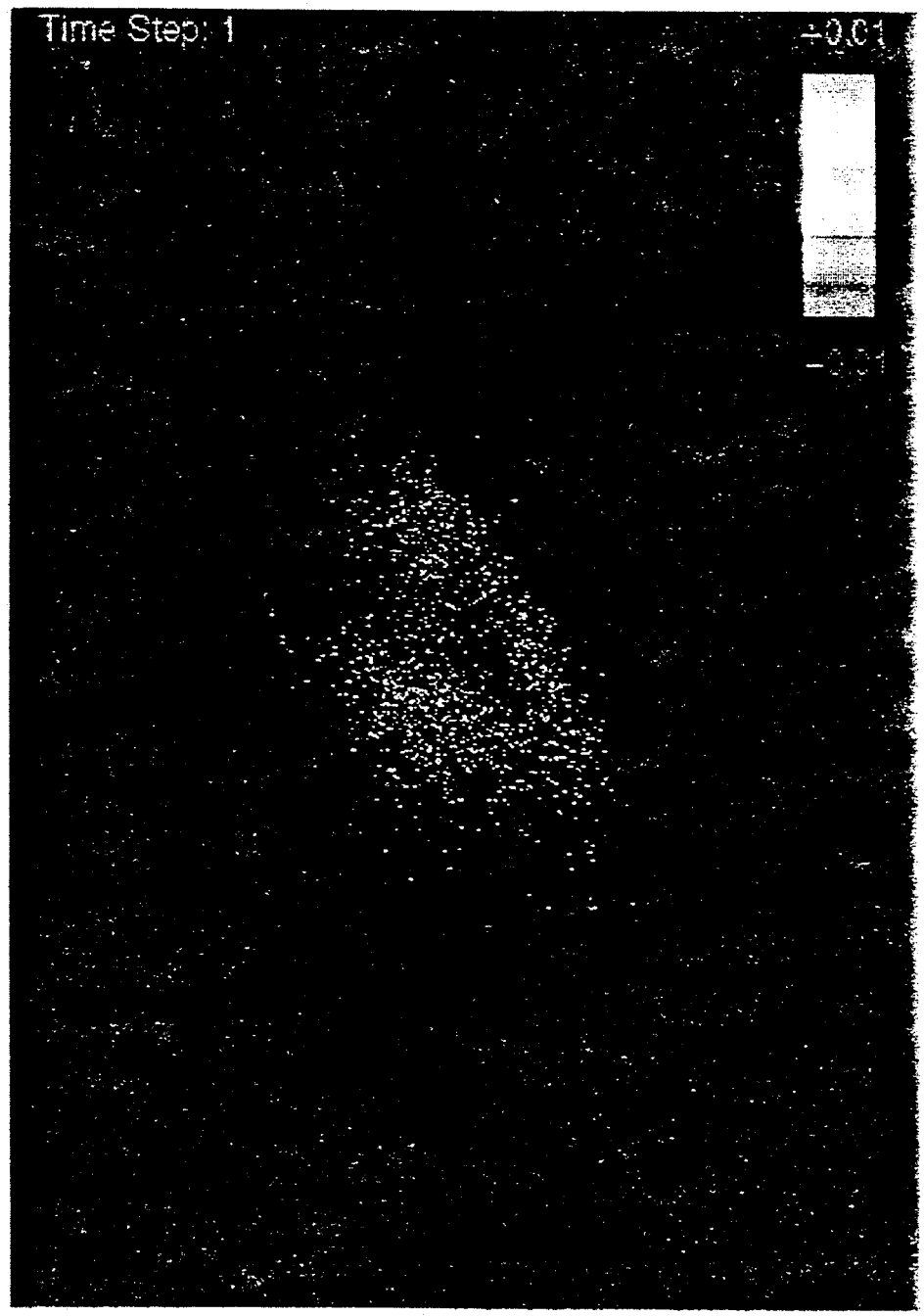
FIGS. 18A and 18B show DTI plots using color to represent a fourth dimension for KRA #9, a human heart transplant recipient with biopsy-proven diagnosis of resolving rejection.
Figure 18B:
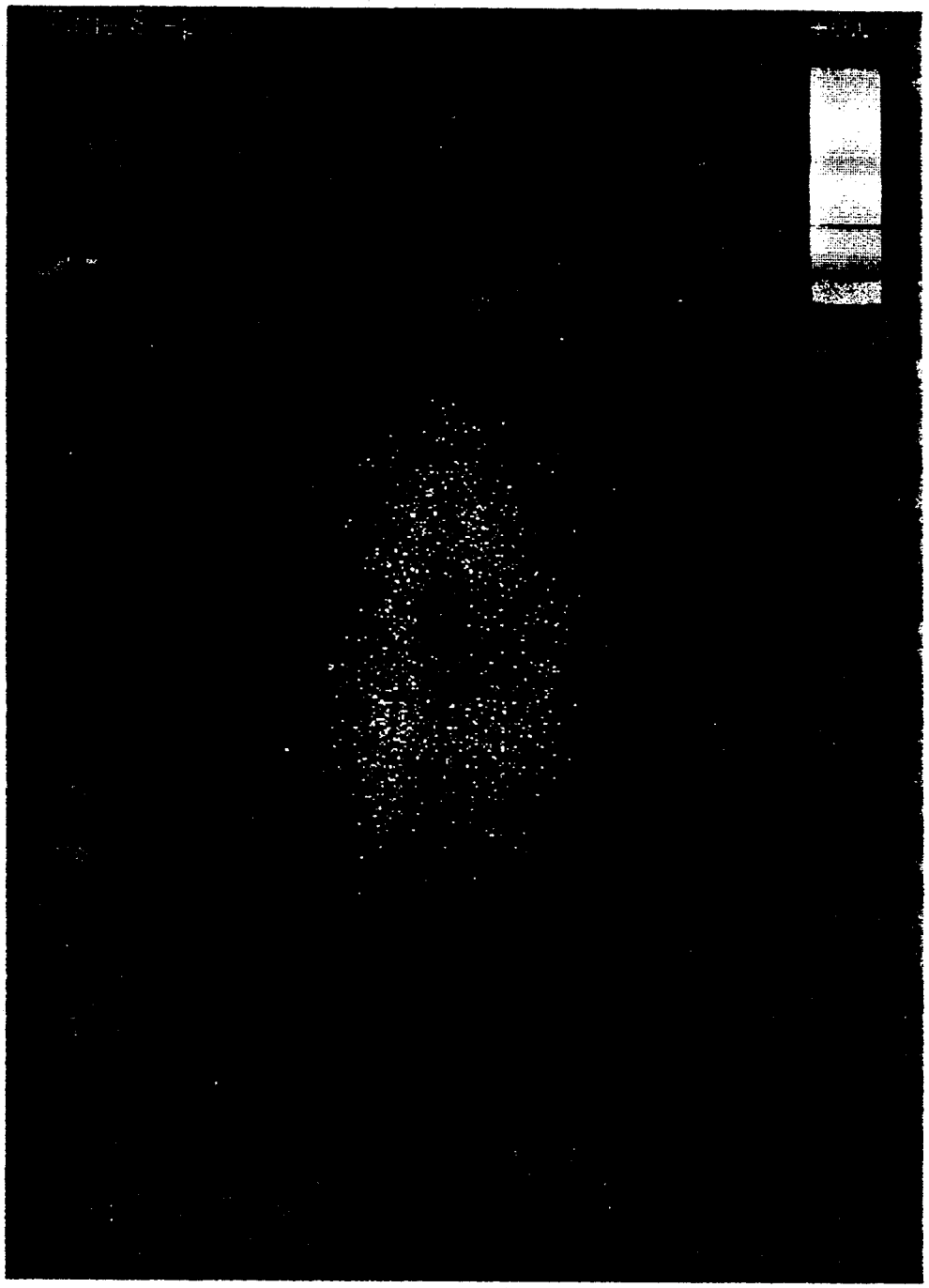

Alternatively, the graph can be centered around the origin by plotting the difference between two RR intervals as a function of the next difference. This type of plot is called a Differential Time Interval (DTI) plot. Graphs of this type are shown in FIGS. 12-15, to be described more below. FIGS. 6A and 6B illustrate the method of this alternate and preferred method of plotting. RR(n), RR(n−1) and RR(n+1) are read (60, 62, 64) from the RR output file. The difference between successive RR intervals, dRR(n), is then calculated (66, 68). dRR(n) denotes the nth difference between successive R waves. dRR(n) is plotted on the x axis (the x variable) and dRR(n+1) on the y axis (70) (the y variable). The variable n is incremented (72), and the process is repeated. The x-y plot provides a two dimensional look at the interval data. Further dimensions can be obtained by adding additional "delays." For example, the plotting illustrated in FIGS. 6A and 6B can be made three dimensional (x-y-z), by calculating dRR(n+2)=RR(n+2)−RR(n+1), and using this for the z variable, to create the point (dRR(n),dRR(n+1),dRR(n+2)) for plotting. A fourth dimension can be provided by adding the variable dRR(n+3), and so on. Examples of multidimensional plots of this type are shown in FIGS. 18A and 18B. More information on DTI plotting can be found in Babloyantz, 1988, in "Does God Play Dice? The Mathematics of Chaos," by Stewart (e.g. pages 183-191), and in "Chaos—Making a New Science" by Gleick (e.g. pages 262-267).

Attractors

As will be described in more detail below, DTI plots provide a geometric representation of the pattern of heart beats over a long period of time. The geometric figure is called an "attractor," because over time, any data point that starts near the attractor gets closer and closer to it.

An attractor provides a qualitative description of all possible "states" of a system, be it a chemical reaction or the cardiac rhythm generator, over an extended period. Systems with different dynamics produce attractors with different shapes. For example, consider the behavior of the pendulum of a grandfather clock. In the first second, the pendulum swings from right to left. The next second, it returns. The motion may be described geometrically by plotting two variables: x, the displacement of the bob from vertical, and y, the velocity. The first portion of the pendulum's cycle describes the bottom half of a circle. The second portion of the cycle, which proceeds along the same path as the first but in the opposite direction, traces the top half of a circle. The sum of these two motions, back and forth, produces a circle, which represents the attractor for a periodic system. A circle seems apt for describing the behavior of the pendulum: each time the bob returns to its initial position, we return to our starting point on the circle.

Figure 24A:
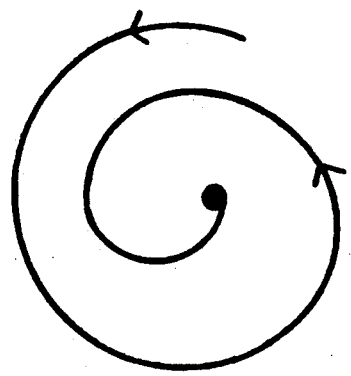
FIGS. 24A and 24B illustrate attractors for undamped and damped pendulums, respectively.
Figure 24B:
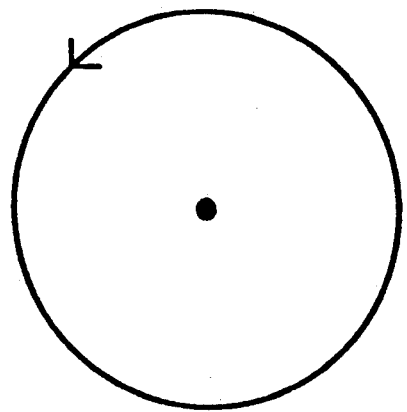

If friction is added to the pendulum's motion, it eventually comes to rest in a vertical position. The attractor for this system, which is called a damped periodic oscillator, is a fixed point (FIG. 24B). Thus the change in dynamics produced by adding friction to the system results in a significant change to the appearance of the attractor. In essence, the shape of the attractor provides a geometrical description of certain "rules" that determine the long-term behavior of a system. Any change in the rules produces a change in the system's dynamics, which, in turn, results in an attractor with different geometry.

Figure 25:
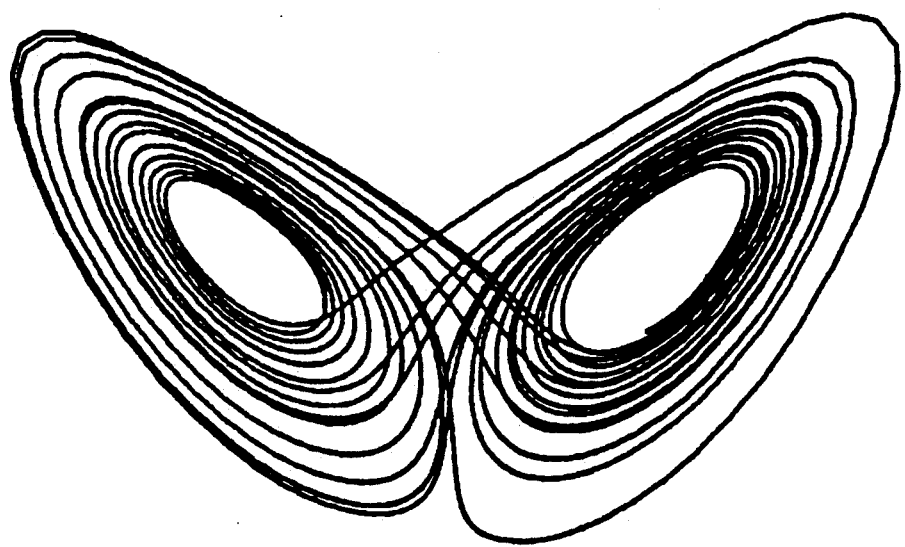
FIG. 25 illustrates a Lorenz attractor.

Certain systems, such as the Lorenz system of equations, demonstrate complex, seemingly random, behavior called chaos. According to the taxonomy of dynamical systems, the attractor for a system whose behavior is non-random and aperiodic is called "strange." The phase portrait for the Lorenz attractor resembles a butterfly, with two great wings emerging from the center of the graph (FIG. 25). The structure of this attractor is far more complicated than the structure of the periodic attractor whose behavior is repetitive and predictable.

Like the Lorenz attractor, the attractor for the non-rejecting heart demonstrates an intricate, coherent structure. Unlike the Lorenz system, we are unaware of the rules that determine the shape of the attractor for the transplanted heart. Identifying these rules is difficult, if not impossible. Our task in diagnosing rejection is far simpler, though. Instead of attempting to elaborate a set of rules, we need only recognize that the rules have changed. The present invention surmises that a healthy, non-rejecting transplanted heart operates under one set of rules, and that these rules, whatever they may be, change with the onset of graft rejection. The change in rules results in a dramatic change in the shape of the cardiac attractor, which may be appreciated by studying the phase portraits for the heart.

On Phase Space Reconstruction and Dimension

We can reconstruct an attractor from a time series in a way that is independent of the precise quantity that is being measured. We need measure only one variable, provided that variable is important to the system under study. In the case of the pendulum, serial measurements of the bob's angular displacement (the x variable described above) provide a suitable time series. For a geometric reconstruction of the dynamics of cardiac rhythm, a series of RR intervals seems an appropriate choice. Once we have settled on an observable, it is critical to establish the number of variables, or dimensions, that determine that system's behavior, so that we may reconstruct faithfully the attractor for the system. According to Farmer et al. (1983), dimension provides, in some way, the amount of information necessary to specify the position of a point on an attractor to within a given accuracy. In the example of the pendulum, knowledge of two variables, position and velocity, provides complete information about the state of the pendulum at any moment. The structure of the pendulum's attractor may be appreciated readily on a two-dimensional plot.

Unlike the pendulum, many systems are characterized properly only by four or more dimensions. For example, specifying the "state" of a five-dimensional system at a given time requires looking at the data from five different vantage points simultaneously. As one might imagine, projecting a five-dimensional system onto a three-dimensional graph produces a confusing picture of the system's dynamics. Instead of seeing an organized "structure," one merely sees randomly scattered points. Points that should be far away from one another wind up being piled on top of one another. It is virtually impossible to study the dynamics of high dimensional systems geometrically.

Figure 26A:
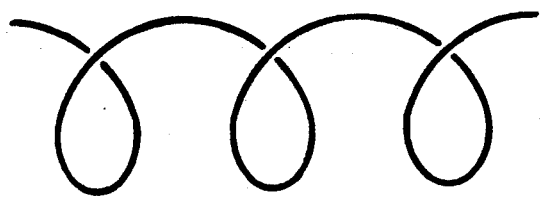
FIGS. 26A, 26B and 26C illustrate the effect of viewing a rope in three different embedding dimensions.
Figure 26B:
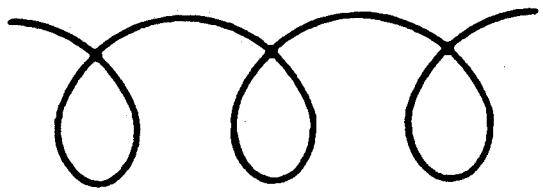
Figure 26C:

Even if a system is merely one dimensional, it may require projection of the system into higher dimension to appreciate properly the spatial relationships between points. Consider a rope that is coiled on itself (FIG. 26A, 26B and 26C). The rope, because it is merely a line when it is uncoiled, has a dimension of one. Since the rope is coiled, however, we must view it in three-dimensional space to appreciate that the line never intersects itself. If we project the coil to a two-dimensional space, the line appears to have self-intersections of dimension 0, i.e., points (Brown, et al. 1991). If the coil is projected to one-dimensional space, the regions of self-intersection become line segments. The goal is to project, or embed the attractor into space of sufficiently high dimension so that all self-intersections are avoided. In other words, when an attractor is embedded properly, points that are truly far away from one another in phase space remain far away from each other. Too small an embedding dimension causes the attractor to fold on itself, giving the illusion that certain points are closer to one another than they really are.

Determining the number of dimensions needed to describe a system is difficult. A variety of algorithms have been published that compute dimension from time series data. These algorithms, which emerge from research in the fields of mathematics and physics, are suitable only for large data sets ($10^6$ points). Since the data sets used in the present invention are of more modest size (N<1200), the invention relies on visual inspection of the phase portrait for the cardiac attractor to draw preliminary conclusions about its dimension.

A computer program can be used to create multidimensional phase portraits that can be rotated in space. When the cardiac phase portraits are plotted in three-dimensions, the spatial relationship between points becomes clearer, compared with a two-dimensional view. Importantly, data points aggregate into coherent structures such as X- and leaf-shapes when viewed in three-dimensional space (FIGS. 18-20). This finding suggests that the cardiac attractor may be low dimensional.

In addition to insights on the long-term dynamics of the heart, the DTI plots reveal information about the cardiac rhythm over brief time intervals. Each point represents a snapshot of the relationship between the current and the next dRR. For example, a point in the right upper quadrant of the graph indicates successive accelerations in heart rate, while a point in the left upper quadrant signifies an acceleration followed by a deceleration. Certain sequences of heart beats are seen commonly. For example, a deceleration followed by an acceleration in heart rate is seen more frequently than successive accelerations.

DTI plots may be constructed not just for single delay differentials, but for any delay desired. For example, for a delay of ten (10), $dRR(n)=dRR(n)-RR(n-10)$, $dRR(n+1)=RR(n+1)-RR(n-9)$, and so on for higher dimensional plots. It is unknown what the optimal temporal delay "T" is for viewing and analyzing heart rate interval data. If T is too small, then $dRR(n)$ and $dRR(n+T)$ are essentially the same measurement. If T is too large, then $dRR(n)$ and $dRR(n+T)$ are random with respect to each other (see Brown, et al., 1991). In most cases, the optimal lag depends on the dynamics of system being studied. For some time series, a strong relationship between successive measurements is retained even with large values for T. In other instances, a minimal increase in T renders the relationship between successive observations random. In general, the present invention used delays between one and five for the purposes of graphical analysis.

Figure 19A:
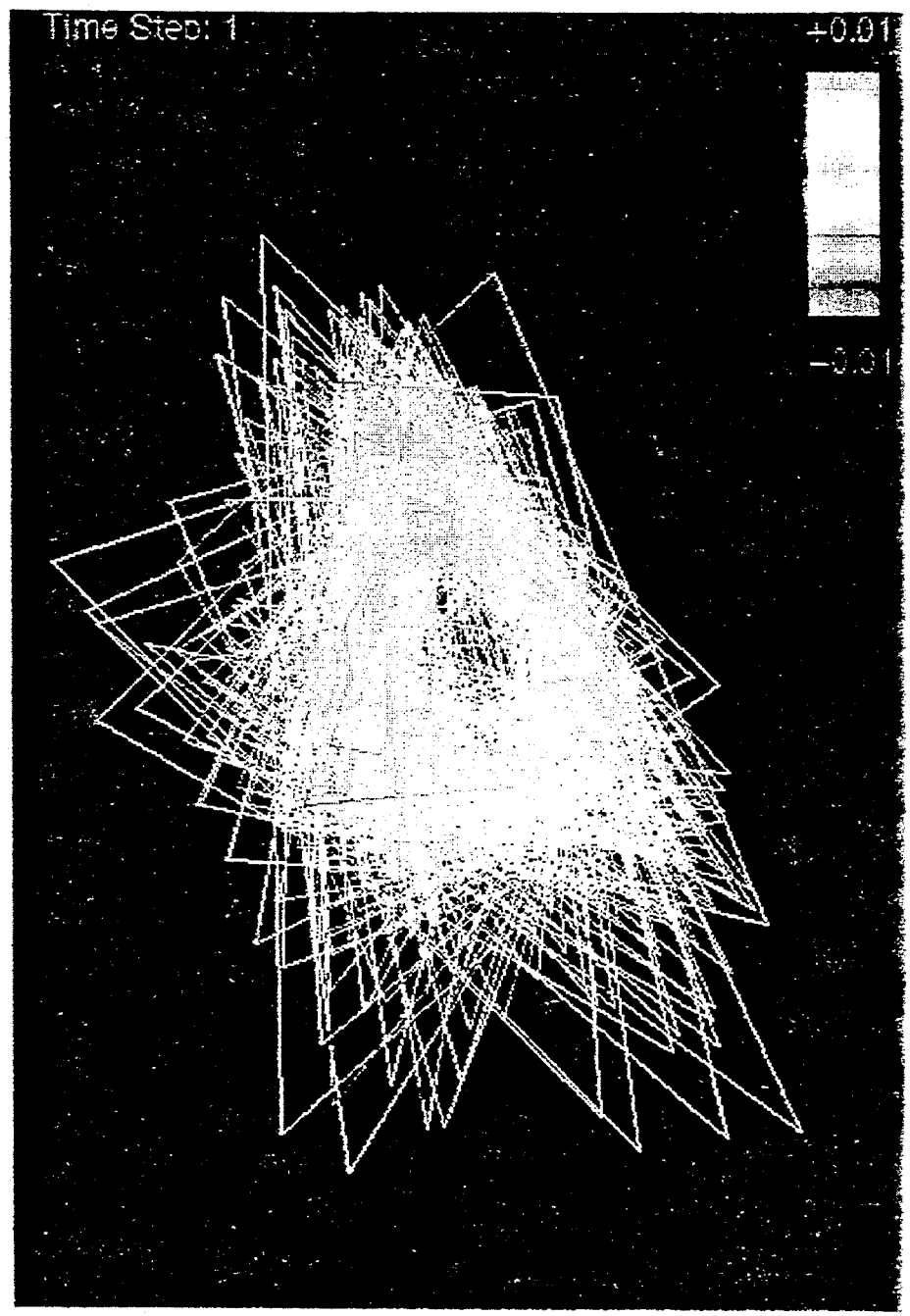
FIGS. 19A and 19B show flow diagrams corresponding to those of FIGS. 18A and 18B.
Figure 19B:
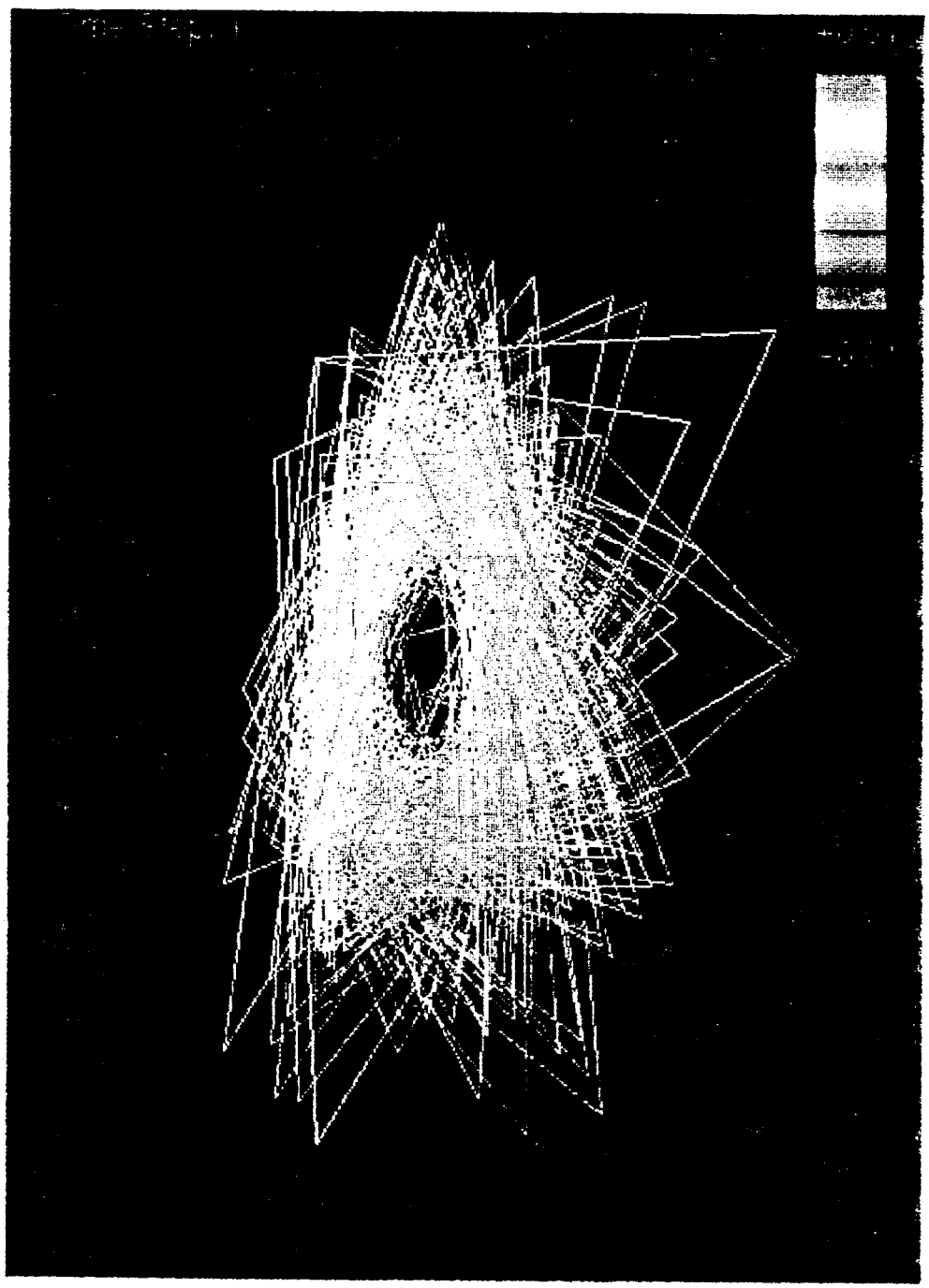

While the DTI plot provides a great deal of information about the long-term behavior of cardiac rhythm, it does not show the temporal relationship between beats, i.e., which came first, second, etc. However, if the points on the DTI plot are connected in the order in which they are recorded, the evolution of interbeat intervals can be followed over time. While this can be done in a two-dimensional plot, plots of three and higher dimensions provide an enhanced reference point for evaluation. Examples of these higher-dimensional plots are shown in FIGS. 18A and 18B, in which the x, y and z variables are obtained from $dRR(n)$, $dRR(n+1)$ and $dRR(n+2)$, as illustrated and explained with reference to FIGS. 6A and 6B. FIGS. 18A and 18B show four-dimensional data for patient KRA-9 from two-different vantage points. This study coincided with a biopsy-proven diagnosis of resolving rejection. In FIG. 18A, the z axis is horizontal to the plane of the drawing. In FIG. 18B, the z axis is vertical and parallel to the plane of the drawing. FIGS. 19A and 19B correspond to 18A and 18B, with sequential data points connected by a line. The line transforms the phase portrait from a "map" to a "flow." The lines, also referred to as orbits, enable one to follow (more readily) the "flow" of data points over time.

In FIGS. 18A, 18B and 19B, color provides the fourth dimension. The phase portrait depicts the variables $dRR(n)$, $dRR(n+1)$, $dRR(n+2)$, $dRR(n+3)$. The preferred color coding scheme is consistent from one phase portrait to another, allowing portraits to be compared from one patient to the next. Colors range from red for large changes in dRR across the spectrum (orange, yellow, green, indigo, violet) to blue for small changes in dRR. The colors enable one to better apprehend the relationships between points on the attractor.

Figure 20A:
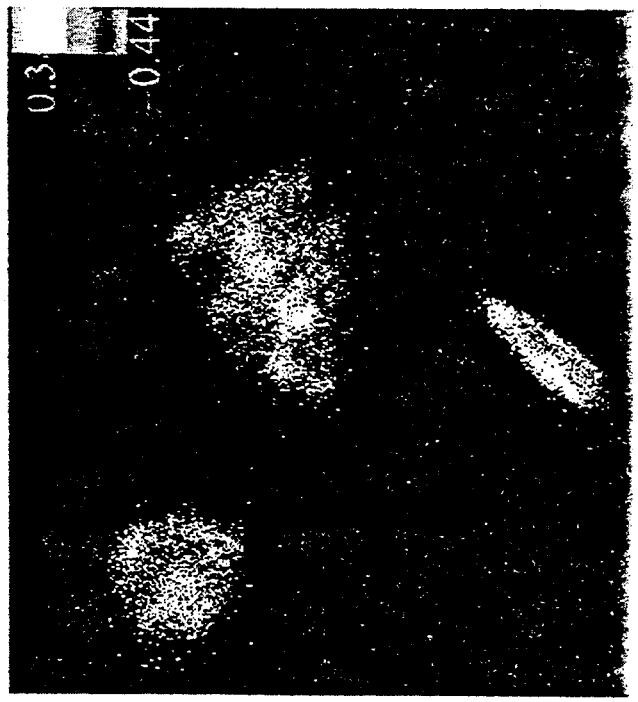
FIGS. 20A and 20B, 20C and 20D show a four-dimensional color DTI plot for a single data set, from four different perspectives.
Figure 20B:
Figure 20D:
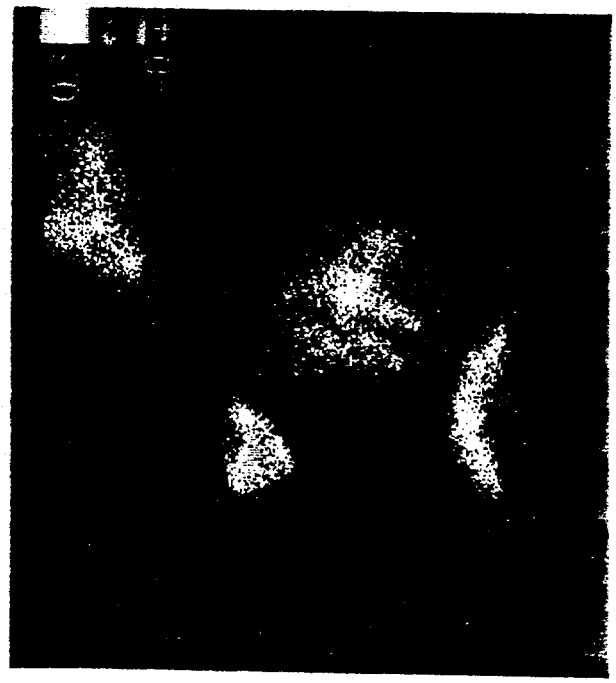
Figure 20C:
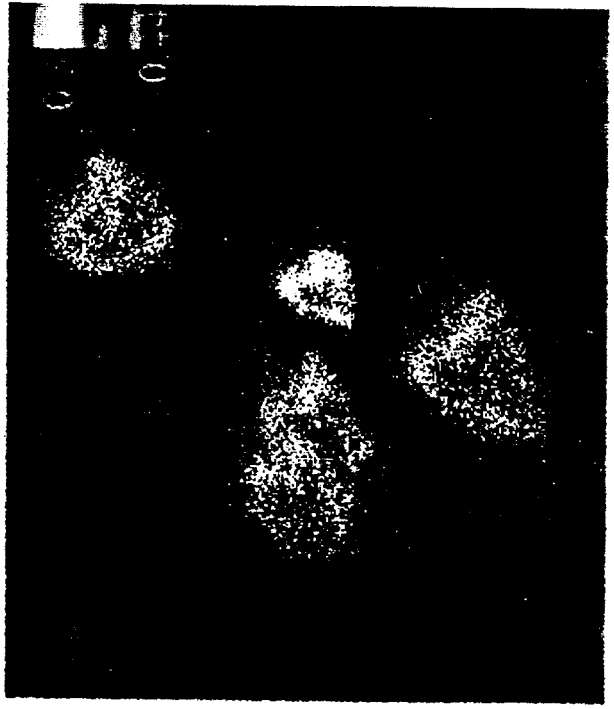

The present invention also provides that the DTI plots be graphed on a color (or monochrome) monitor in a "motion picture" sequence, to allow an observer to see the pattern of points or trajectories (orbits) develop over time. In the case of a map of a phase portrait, the motion picture sequence preferably illustrates the movement of a "worm," or line segment, 10 data points in length traversing through the data set. The path followed by the worm traces the trajectory of a series of orbits around the attractor. Other examples of four-dimensional DTI plots are shown in FIGS. 20A, 20B, 20C and 20D, which are four different views of the same data set for a non-rejecting human patient HOR. These phase portraits illustrate the advantage of viewing the data in three dimensional space. Viewed along the x-y plane, as shown in FIG. 20A, three distinct clouds of points are discernable, one centered around the origin, the remaining two at 6 and 10 o'clock, respectively. When the plot is rotated, as shown in FIG. 20B, a fourth cloud of points appears in the right upper quadrant. For the purposes of this discussion, this cloud is designated the "gold" cluster. It is used to understand the rotation of the attractor in phase space. In FIG. 20C, the "gold" cluster in the right upper quadrant of FIG. 20B is visible in the lower center of the phase portrait. In FIG. 20D, the "gold" cluster has rotated to the left upper quadrant. The pattern seen in this phase portrait is produced by the following sequence of heart beats: normal (nl) interval--nl--premature beat--compensatory pause--nl---nl. The premature beat in this instance was a normal sinus beat, not a premature ventricular contraction. The essential element is that the beat was relatively premature compared with the preceding two intervals. As with the example of the coiled rope, the relationship between nearby points on the attractor becomes clearer when the phase portrait is viewed from various vantage points in three-dimensional space. When a fourth dimension (color) is added, the distinction between points becomes even clearer. When viewed in two dimensions, as in the DTI plot, the relationship between successive beats is obscured, as the object is folded over on itself.

Figure 7:
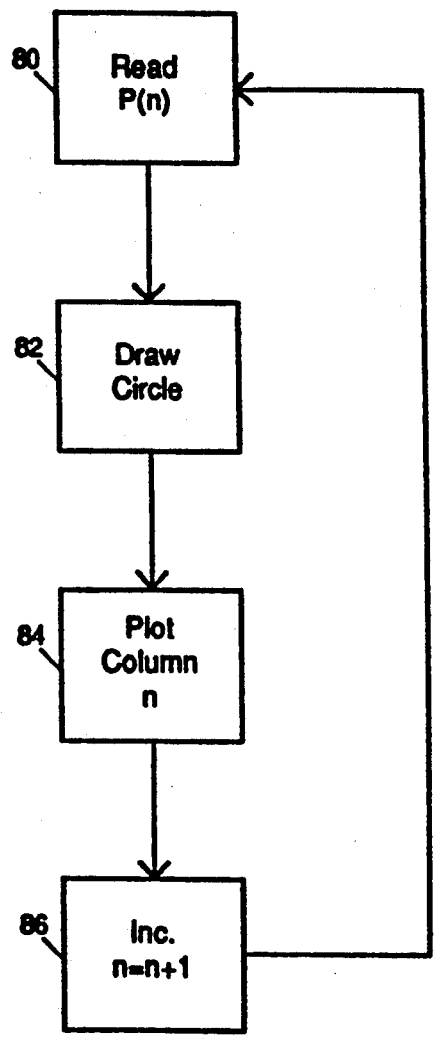
FIG. 7 is flow chart of the recurrence plotting technique according to the present invention.
Figure 16A:
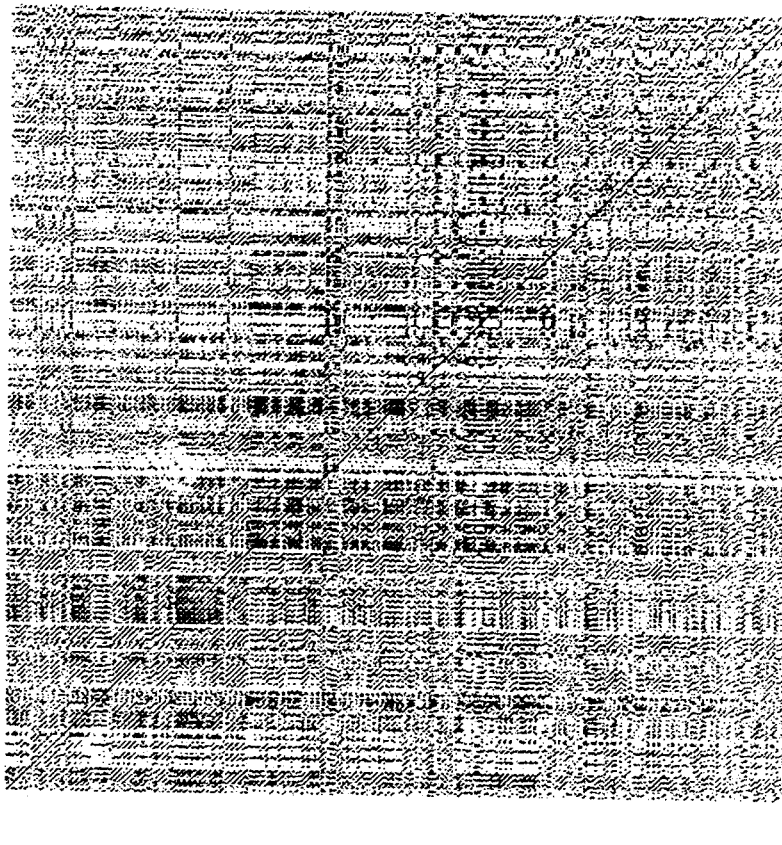
FIGS. 16A and 16B show recurrence plots for a canine patient with and without rejection, respectively.

Another graphical device, recurrence plotting 42, enables placement of points in chronological order. Like the "worm" traversing through the attractor, the recurrence plot allows for an appreciation of the temporal relationship between successive points. The recurrence plotting method is illustrated in FIG. 7. To make a recurrence plot, the first DTI point, P(n), is read (80), and a circle is drawn around it (82). The circle must encompass at least a predetermined percentage of points, for example 10% of the points, as used in the present invention, in the data set of N points. Next (84), each point in the data set is analyzed to determine if it falls within the circle. If it does, a point is placed in a column corresponding to the point. If it is the first point, the column is the first column, and so on. If point 250 of N is in the circle around point 1, then a point is plotted in row 250 of column 1. If point 975 is in the circle around point 651, then a point is plotted in row 975 of column 651, and so on. The variable n is incremented and the procedure repeated until all points have been reviewed and plotted. An example of a recurrence plot for a non-rejecting canine heart is shown in FIG. 16A, and for the same heart during rejection in FIG. 16B. As with DTI plots, a change in the recurrence plot coincides with histologic diagnosis of rejection.

One method for quantifying the change in the pattern of heart beats is called redundant or mutual information. Mutual information measures the estimated joint probability distribution of two variables. Information may be any symbol or sequence of symbols, such as letters, musical notes, or numbers. In the present case, the information is the time interval between heart beats.

Calculating mutual information allows consideration of the question: given a measurement of the RR interval now, how much on average can be predicted about the next interval? If the amount of mutual information is large, we can predict the next interval with great confidence. In other words, the experimenter would only need to record the EKG for a few heart beats to have complete information about the dynamics of that heart. On the other hand, if mutual information is small, new measurements are required constantly to update the knowledge of the observer. More information on mutual information can be found in Fraser and Swinney, 1986, and Fraser, 1989. Andrew M. Fraser and Harry L. Swinney, "Independent coordinates for strange attractors from mutual information," Physical Review A, vol. 33(2) 1986, pp 1134–1140. Andrew M. Fraser, "Information and Entropy in Strange Attractors," IEEE Transactions on Information Theory, vol. 35(2) 1989, pp 245–262.

Figure 8:
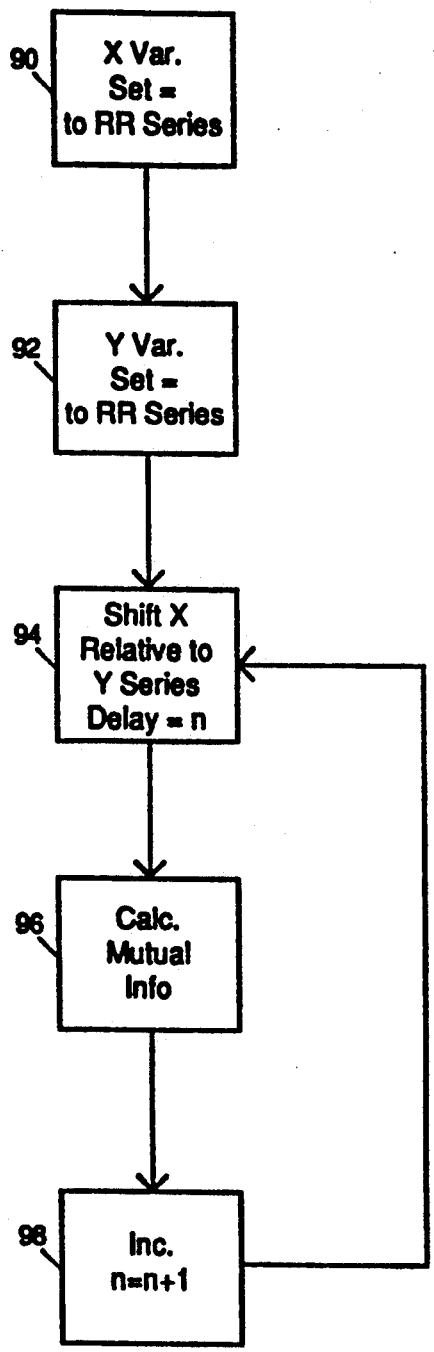
FIG. 8 is a flow chart showing a method for determining mutual information.

An example of mutual information entails the use of RR intervals and the method of delays. It is illustrated in FIG. 8. As explained above with respect to FIGS. 4B and 4C, the series of RR intervals from the RR output file serves as the x variable (90). The y variable is created using a duplicate of the x variable (92). The "delay" is created by shifting (94) the entire y column relative to the x column.

Mutual information is calculated (96) for delays between 0 and 100. Naturally, mutual, information is highest when the delay equals zero. The two columns are aligned, and if we know the value of x we have complete knowledge of the value of y. Once a delay is introduced, we are less certain of the y value, and mutual information decreases. The decrease continues with successively longer delays until a minimum is reached. R. S. Shaw (cited in Fraser 1986 as "personal communication") has recommended that this minimum be used to represent the amount of mutual information in a system.

Figure 9:
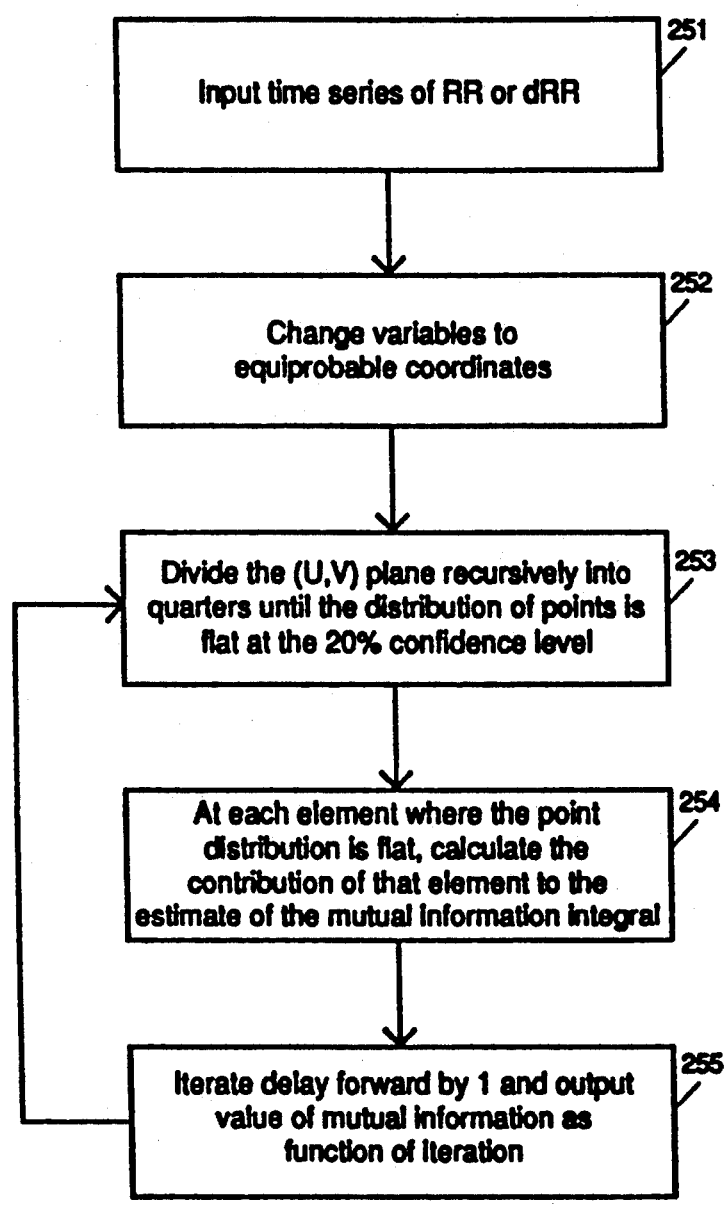
FIG. 9 is a flow chart showing further methodology for computing mutual information.

FIG. 9 shows the algorithm for calculating mutual information. The time series of RR or dRR intervals is input for analysis (251). The variables are changed to equiprobable coordinates on the u,v plane (252). The (U,V) plane is divided recursively into quarters until the distribution of points is flat at the 20% confidence level (253). At each element where the point distribution is flat, the contribution of that element to the estimate of the mutual information integral (254) is calculated. The iterate delay is forwarded by 1 and the value of mutual information integral is output (255). The process is then repeated starting at step 253. A copy of a computer program for calculating mutual information using this algorithm may be obtained from anonymous FTP on the Internet computer network. The Internet Protocol address is: chaos.utexas.edu. A copy of this program is set forth at the end of the specification. The modules of this program include SCODE, INTERLEA, POLLY, EKBIN (to convert ASCII data to binary), and JL2 (shellscript for linking these programs and computing mutual information for two dimensions).

As shown in the example given below, the amount of mutual information in the case of rejection is high as compared to a non-rejecting heart. In other words, the predictability of the interbeat interval increases during rejection; the interval tends to vary much less from one beat to the next. On the other hand, the non-rejecting heart shows a low degree of mutual information, making it difficult to predict the interval of a heart beat from the preceding one.

As stated previously, variations in RR intervals in heart transplant recipients are imperceptible without high precision electronic measurements. The precision, or sampling resolution required, depends on the species being studied. In the majority of canine heart transplant recipients, an EKG sampling rate of 1 KHz (sampling resolution=1 millisecond) was adequate to capture the subtle changes in RR and dRR interval patterns seen in non-rejection and rejection. In contrast to the sampling resolution required to diagnose rejection in canines, a much greater sampling resolution is required to arrive at an accurate diagnosis in human transplant recipients.

FIGS. 23A and 23B demonstrate the effects of sampling rate on the resolution of DTI plots. FIG. 23A shows data for human patient GEN#2 obtained at 10 KHz, while FIG. 23B shows the same time series sampled at only 1 KHz. Both plots demonstrate clearly the boundaries, or range, of heart beat intervals for this patient. The overall shape, or profile in each plot resembles a triangle with a small oval window removed from the center. The 1 KHz plot, however, fails to reveal subtle changes in the pattern of heart beats over time. Although 750 points are plotted in both figures, less than 300 discrete points appear in the 1 KHz plot. The remaining points are hidden from view, lost because of the low sampling rate. In contrast, the 10 KHz (resolution=100 microseconds) data preserves the fine details of the heart rate data. Instead of a virtually homogeneous distribution of points, the point distribution features varying textures and densities. It is obvious that many points are clustered in the lower left quadrant of the graph. Since the start of the clinical trials used to develop the present invention, it has been established that sampling rates of about 10 KHz or greater must be used to capture the intricacies of heart rate patterns over time for humans. It is believed that higher sampling resolution is required in humans because of differences in receptor density on the heart surface, as well as size differences between species. The invention is applicable to diagnosing rejection in mammals other than dogs or humans, but the appropriate mimimum sampling rates required may be different.

Referring back to FIG. 4A, the methods of diagnosis of the present invention will be described in more detail. Diagnosis 41 uses visual analysis to compare the pattern of a baseline DTI or other method of delays plot to a current measurement, and detect changes or shifts. Certain changes or shifts indicate rejection, and in particular a change or shift showing a reduction in interbeat variability. Diagnosis 41 can also be done automatically using software that can compare the baseline pattern to subsequent patterns to detect shifts or changes toward a pattern indicating rejection.

Diagnosis 43 can also be done by comparing current recurrence plots to baseline measurements. Once again, shifts indicating a change in the pattern of heart beats over time indicate rejection. Such analysis can be done by visual inspection, or by computerized pattern analysis.

Mutual information rejection diagnosis 45 indicates rejection whenever mutual information changes significantly as compared to a baseline measurement for the patient under testing. Currently, the doubling of mutual information from the baseline is used as an indication of rejection. However, other thresholds or combinations of thresholds could be used.

A variety of quantities can be computed to characterize a dynamical system, including dimension, Kolmogorov-Sinai entropy, and Lyapunov exponents. Any or all of these quantities may provide a more complete understanding of the change of dynamics associated with rejection. For example, the dimension of the cardiac attractor may decrease with rejection.

Finally, rejection diagnosis 47 can be used to automatically diagnose the onset or presence of rejection in a transplanted heart based on the weighting of variables obtained from a neural network that is "trained" to recognize patterns indicating rejection. The weightings obtained from the "learned" neural network can be used to identify rejection from patterns of input data.

Figure 10:
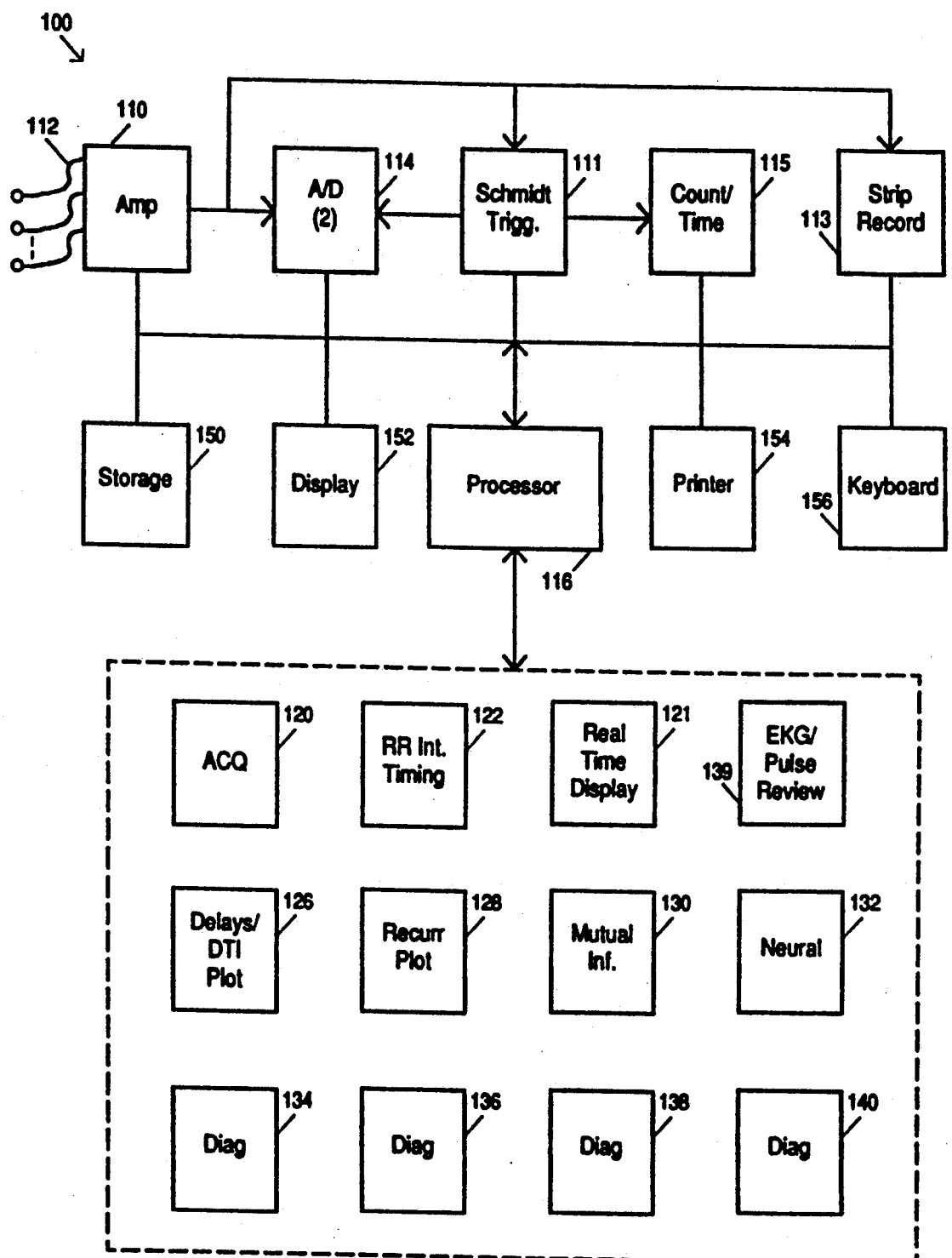
FIG. 10 is a simplified block diagram of the monitor and diagnosis unit 100 according to the present invention.

Referring now to FIG. 10 there is illustrated the heart rejection monitor and diagnostic unit 100 according to the present invention. Monitor and diagnostic unit 100 includes a low-noise, high-gain preamplifier 110. Self-adhesive disposable Ag/AgCl electrodes 112 (at least one pair) are provided to attach to the patient's skin to feed signals from the patient's heart to amplifier 110. One of two analog to digital (A/D) converters 114 (preferably a model CIO-AD16Jr, manufactured by Computer Boards, Inc., of Mansfield, Mass.) receives input from the preamplifier 110. A processor 116 is provided and operates under the control of software modules 120–140. Software 120–140 is preferably stored on magnetic media, generally represented by storage 150.

A Schmidt trigger 111 is also connected to receive the amplified EKG. Trigger 111 is set to send a pulse to counter/timer 115 (preferably a CIO-CTR05 5 channel 16 bit counter/timer board, also available from Computer Boards, Inc.) each time it detects the upstroke of the QRS complex. The counter/timer 115 times the interval between pulses and produces a series of digital measurements of interbeat intervals. Counter/timer 115 preferably is precise enough to measure the interbeat interval to 4–5 decimal precision (100 microsecond accuracy), at a minimum. According to one mode of operation, the counter/timer includes a continuously running clock (running continuously throughout recording) and a lag clock. The lag clock is started each time a pulse is received from the Schmidt trigger, and reset after it is read. The lag clock and the running clock are polled simultaneously and periodically. If the lag clock value equals zero (i.e. it has not been triggered), then it is polled again later. If the value is non-zero, a TTL pulse must have been sent. The time of occurrence of a TTL pulse can be determined by subtracting the lag time interval from the time on the running clock at the instant the lag clock is read. Once the lag clock has been read, it is reset. The running clock remains running continuously. Knowing the time of occurrence of each TTL pulse with respect to the running clock allows the RR interval to be calculated easily in real-time. The advantage of this method is that it can keep track of both the total recording time (useful especially for 24-hour studies) and RR interval times. A rhythm strip recorder 113 is optionally connected to the amplifier 110 to record the EKG on a paper strip.

Processor 116 operates under the control of acquisition software 120 to control A/D converters 114 for the purpose of digitizing the analog EKG signal received from amplifier 110 at the rate of 250 Hz, and to digitize the pulse train received from the Schmidt trigger. Storage 150, either in the form of magnetic, RAM, optical or other read/write medium is provided to store digitized samples received from converters 114. Preferably, the EKG samples and the pulse train samples are combined into a single data set with a common time frame. Software 122 provides for the real-time acquisition of interbeat interval timings from counter/timer 115 and for their storage in storage 150 in real time to provide an R-R interval output file ("RR output file").

Processor 116 can operate under the control of software 121 to display the EKG and Schmidt trigger pulse train on display 152 (on two different channels), or cause the EKG to be recorded on the strip recorder. EKG/pulse train review software 139 permits the digitized EKG and pulse train to be displayed off-line at a low rate of speed to permit inspection of the pulse train for the purpose of identifying spurious pulses triggered by noise. Software 139 also provides the capability to remove any spurious pulses from the digitized EKG/pulse train file.

Under the control of delays/DTI plotting software 126, processor 116 can perform the plotting described with reference to FIGS. 5, 6A and 6B, sending output to display 152 and/or printer 154. Preferably, display 152 is a high resolution color graphics monitor, and printer 154 a laser printer (black and white or color). Processor 116 performs recurrence plotting as described with respect to FIG. 7 under the control of recurrence plotting software 128, with output selectively sent to the display 152 and/or printer 154. Mutual information software 130 is provided to control processor 116 to achieve the algorithms set forth with respect to FIGS. 8 and 9. Neural network software 132 provides for analysis of the RR interval data and patterns based on predetermined neural network weighting coefficients.

Rejection diagnosis software 134 can perform pattern recognition algorithms of conventional design (in addition to neural network pattern recognition) to compare the pattern of a baseline DTI or other method of delays plot to a current measurement, and detect substantial changes or shifts. If rejection is thus detected, warning may be given by text or other visual indication.

Similarly, processor 116 operates under the control of rejection diagnosis software 136 to detect changes in recurrence plots from a baseline measurement. If a pattern shift is detected by conventional pattern analysis or using neural network techniques, a warning may be given by visual or audible means. Mutual information rejection diagnosis software 138 controls processor 116 to warn of rejection by textual message or visual indication whenever mutual information goes above the predetermined threshold as compared to a baseline measurement for the patient under testing. Finally, rejection diagnosis software 140 is used with neural network software 132 to identify pattern changes diagnosing the onset or presence of rejection in a transplanted heart.

Preferably, monitor and diagnostic unit 110 is built from a standard personal computer or workstation, with the processor 116, storage 150, display 152, printer 154 and input device/keyboard 156 standard components thereof. A/D converters 114, and counter/timer 115 are preferably plug-in boards installed in the computer and attached to the computer's I/O bus. Amplifier 110 and Schmidt trigger 111 are housed in a stand-alone unit, which receives the EKG, amplifies it, and outputs the amplified signal and the corresponding TTL pulses. Also, the stand-alone unit preferably provides optical isolation between the EKG leads and the electronic circuits of the present invention. The stand-alone unit includes terminals for plugging-in disposable electrodes 112 to amplifier 110.

Figure 11:
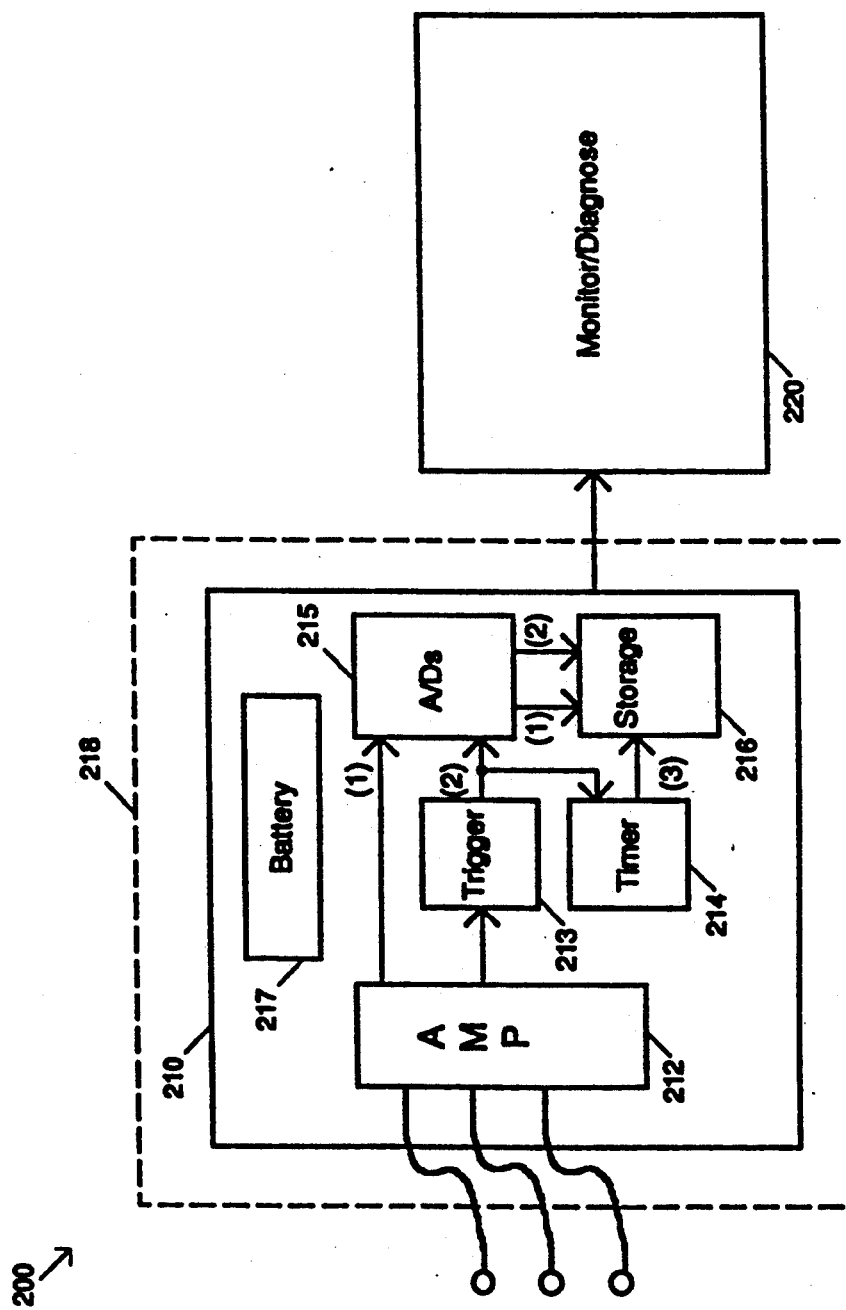
FIG. 11 is a simplified block diagram of an alternate embodiment for ambulatory monitoring according to the present invention.

Referring now to FIG. 11 there is shown an alternate embodiment of the apparatus of the present invention.

According to embodiment 200, there is provided an ambulatory monitor 210 which can be used to record EKGs and heart beat intervals. Monitor 210 includes an amplifier 212 and disposable electrodes 212. A Schmidt trigger 213 detects the upstroke of the QRS and produces a corresponding pulse train to timer 214, which times the intervals between pulses to determine the interbeat intervals. The intervals are timed to 4–5 digit precision. A pair of analog to digital converters 215 are provided to digitize the amplified EKG and pulse output of the trigger 213. The EKG and the pulse output of the trigger are each sampled at a relatively low rate such as 250 KHz or 125 KHz, and recorded on recording device 216, which preferably consists in part of a low power miniaturized disk drive of the type used in lap-top computers. The EKG and pulse train are digitized and saved for the purpose of detecting artifacts in the pulse train caused by false triggers. Because the intervals are separately timed with precision, there is no need to record precisely the EKG or pulse train, but rather only with enough resolution to determine if each pulse properly corresponds to a legitimate QRS complex. Thus, storage requirements are minimal as compared to those required to store the EKG with high resolution.

The interval measurements produced by timer 214 are also stored on device 216. Storage device 216 includes a data formatting circuit which stores the three input signals consisting of the digitized EKG, digitized pulse train and timer intervals so that they can be correlated to one another for the purpose of eliminating artifacts caused by false triggers. Monitor 210 includes suitable user operated controls (not shown) in order to start and stop recording. Unit 210 includes a battery 217 to supply power to the electronic components, and a carrier 218 that can be used to support the unit 220 in an ambulatory position on the patient, for example on the patient's belt.

Once an EKG has been recorded, device 210 can be coupled to an analyzer unit 220, which includes the same analysis and diagnostic components as the monitor and diagnostic unit 100. Unit 220 is used to perform rejection analysis and diagnosis based on the data stored on storage unit 216.

Battery 217 and storage 216 are of sufficient capacity to allow unit 210 to operate for an extended period. Preferably, the unit can continuously measure and record interbeat intervals for a 24 period.

EXAMPLES

Canine Transplant Recipients

Figure 12A:
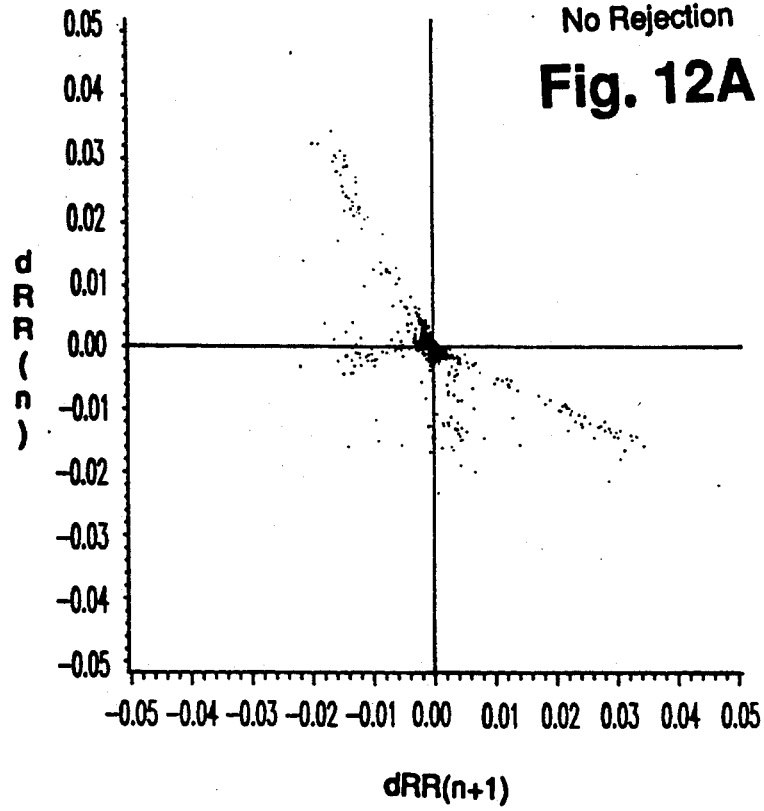
Figure 12B:
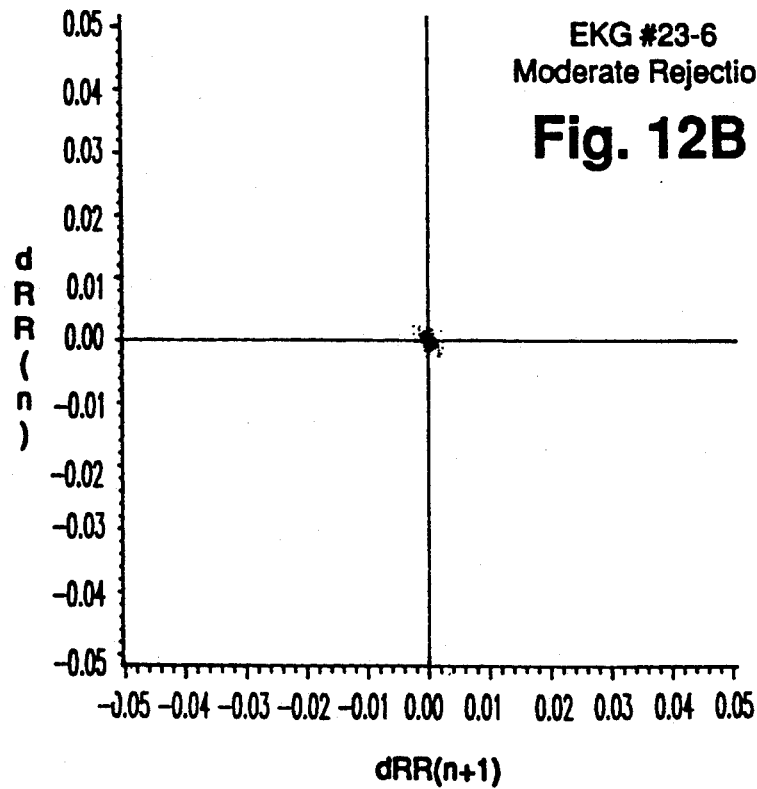

The present invention has been used on both canine and human patients. In the canine studies, daily 15 minute resting EKGs were obtained on eight canine heart transplant recipients. A typical DTI plot for a dog heart transplant patient is shown in FIG. 12A, four days after heterotopic heart transplant. Points are arrayed in an X-shaped pattern. An EMBx showed no signs of rejection. Two days later, following withdrawal of immunosuppression, the pattern changed dramatically, with a vast number of data points coalescing around the origin, as shown in FIG. 12B. A biopsy demonstrated signs of moderate rejection. FIGS. 13A and 13B and 14A and 14B illustrate DT1 plots from other canine heart transplant recipients.

As described above, rejection appears to modify the rules for generating a series of heart beats; the DTI plot makes this change visible without the need for a biopsy. In eight canine transplant recipients, the DTI plot changed markedly in appearance in 9/10 episodes of rejection.

Three to four days after each heart transplant, a "baseline" mutual information was computed using 512 heart beats. The mutual information algorithm was iterated 100 times. After a certain number of iterations, a local minimum for mutual information is reached. Shaw has recommended using this local minimum as one means of quantifying one amount of mutual information in a system. According to the present invention, heart rejection is defined as doubling in mutual information compared to baseline. Using this definition, a sensitivity and specificity of 100% is achieved when compared with the heart biopsy.

FIG. 17 is a table with canine results, showing mutual information for rejection and non-rejection states. The table indicates that a doubling of mutual information diagnoses rejection. The plots in FIGS. 12-15 are labelled to correspond to the canine patients shown in the table of FIG. 17.

Figure 16B:
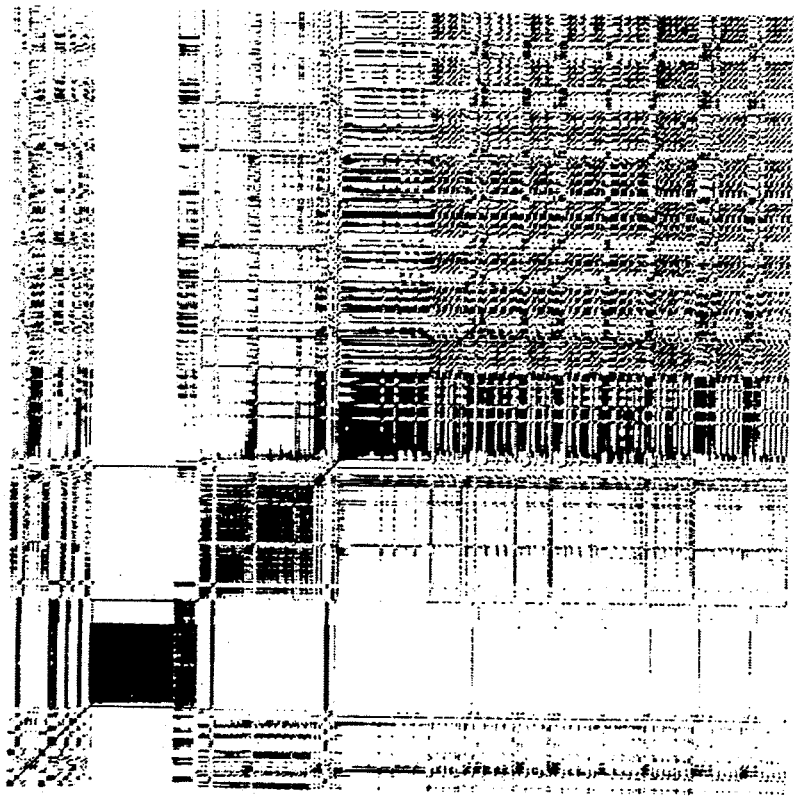

Typical recurrence plots (which use RR intervals as opposed to dRR) for a non-rejecting and rejecting canine heart are shown in FIGS. 16A and 16B, respectively. The patterns are strikingly different. FIG. 16A shows multiple short diagonal lines running parallel to the diagonal line in the center of the graph. Such lines represent successive trajectories that pass near one another in phase space. The phase portrait for this patient (FIG. 14A) shows a band of points surrounding the origin. In contrast, the recurrence plot for the rejecting heart shows several "blocks" of points. The latter picture is consistent with a slow "drift" in the heart rate, as if rejection has eliminated meaningful feedback to that heart's rhythm generator.

Human Heart Transplant Recipients

The present invention has been used on human heart transplant recipients as part of an ongoing clinical trial. Of the 15 patients enrolled in the study thus far, four have shown histologic evidence of graft rejection (four patients, six episodes of rejection). Representative case histories are provided below.

Figure 15A:
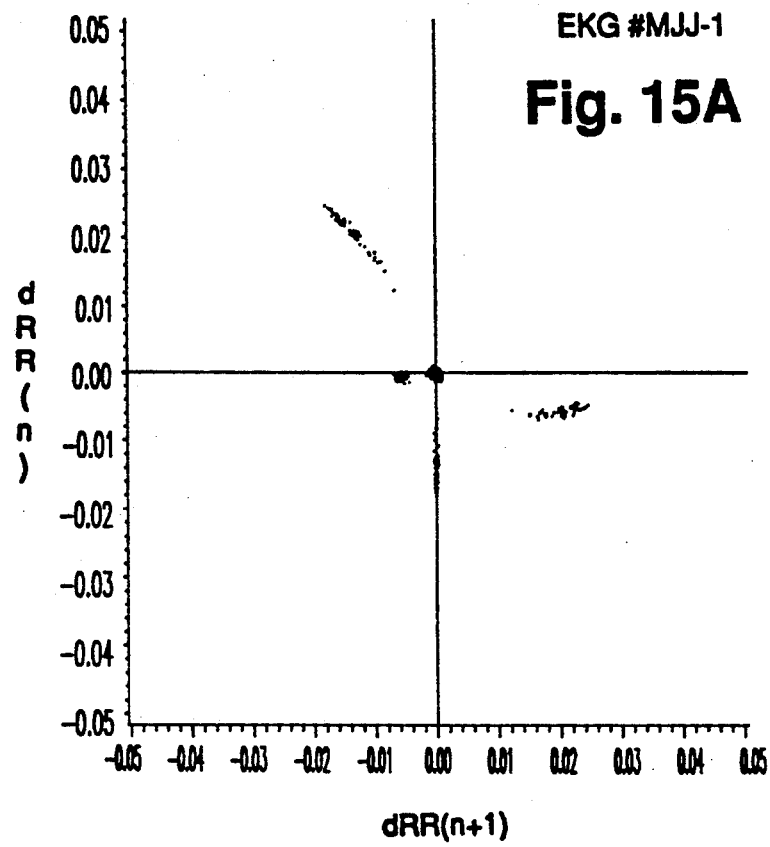
FIGS. 15A and 15B show DTI plots for a human patient before and during rejection.
Figure 15B:
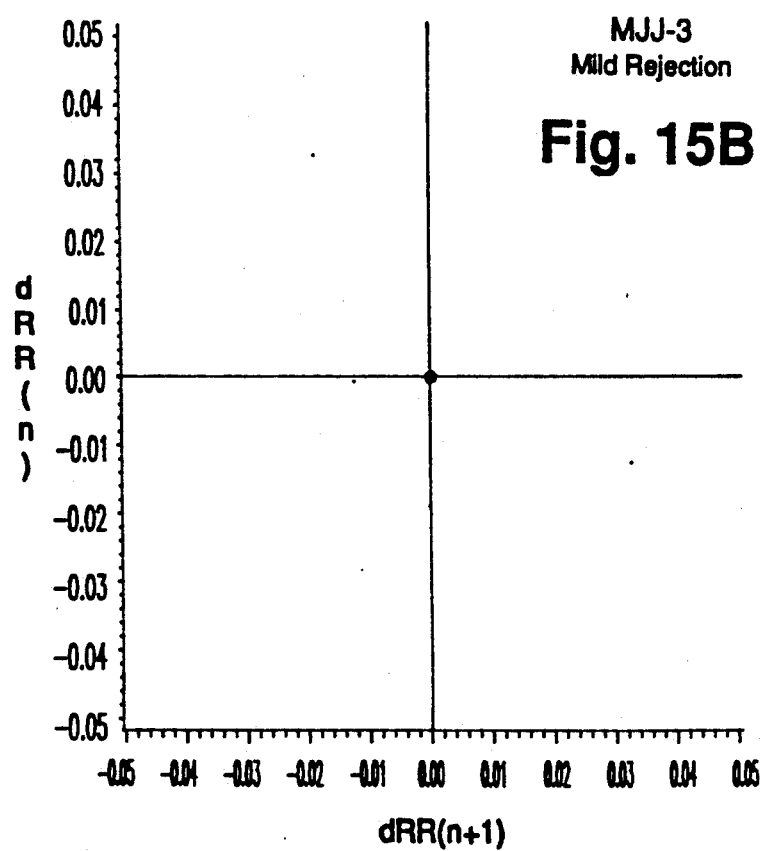
Figure 21A:
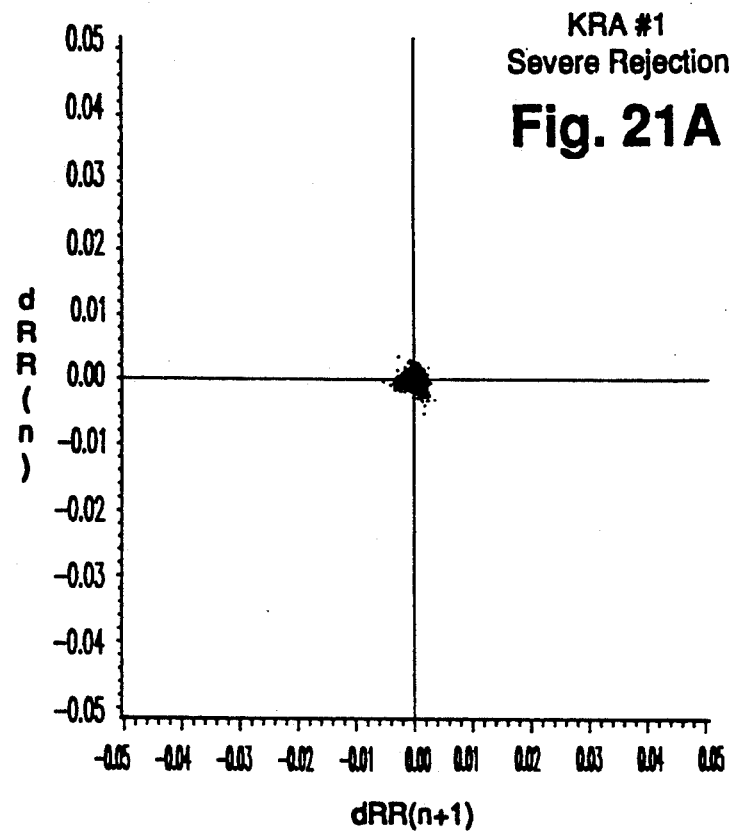
FIGS. 21A and 21B are DTI plots for KRA#1 and KRA #9, respectively, in a human patient showing rejection followed by recovery.
Figure 21B:
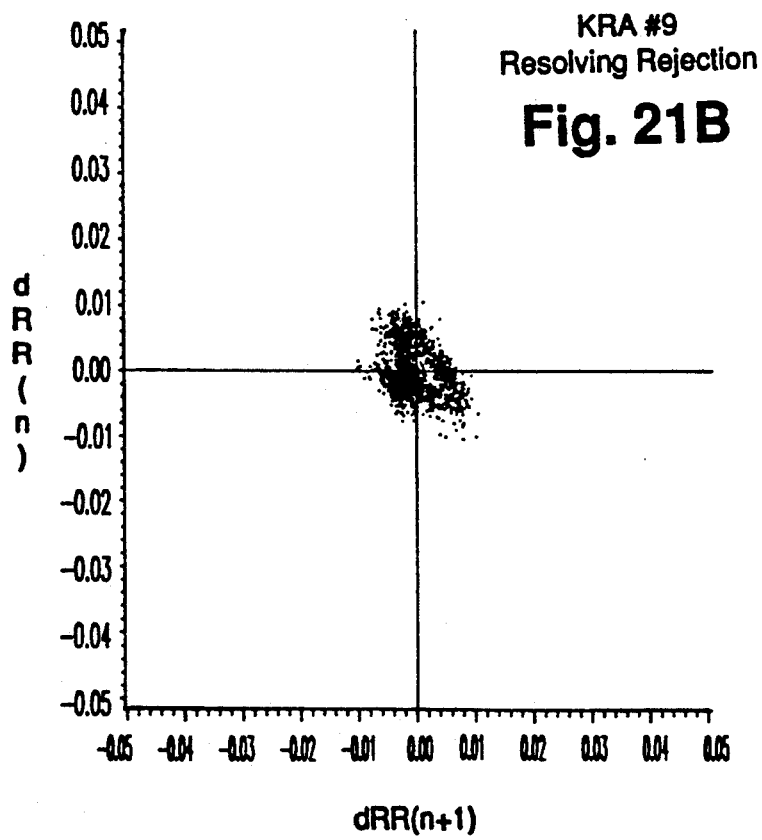

The baseline DTI plot for patient MJJ shown in FIG. 15A obtained three days after transplantation demonstrated an "X-shaped" distribution of points. Roughly 20% of the points occur outside of the central cluster of points. The pattern of heart beats that produces this pattern is normal-normal-premature-compensatory pause-normal-normal. Four days later, as shown in FIG. 15B, the points collapsed around the origin. Not only were the "wings" of the X gone, but the central core of points had collapsed compared with the core from the baseline study. The DTI plot coincided with EMBx showing mild rejection. The patient was started on a three-day course of intravenous (IV) steroids and recovered uneventfully. The first DTI plot obtained for patient KRA (FIG. 21A) showed severe collapse of points around the origin of the graph. EMBx confirmed severe rejection, and the patient was started on a three-day course of IV steroids. On the first day after treatment began, the DTI plot changed markedly, with the area covered by points increasing 10-fold compared with the previous day's study. This suggested a positive response to treatment. The DTI plots continued to show improvement one week later, when a follow-up biopsy was obtained to assess response to steroid therapy. The EMBx was unchanged. Since the patient was doing well clinically, no further treatment was provided. Another EMBx obtained one week later finally demonstrated histologic resolution of the rejection. The DTI plot continued to support a diagnosis of resolving rejection (FIG. 21B). While the DTI plot demonstrated signs of recovery within 24 hours of treatment, the EMBx lagged behind, failing to show resolution of rejection until two weeks after therapy had started. Graphical analysis of the pattern of heart beats as described in this application may detect onset of, and recovery from, rejection more rapidly than EMBx.

Figure 22C:
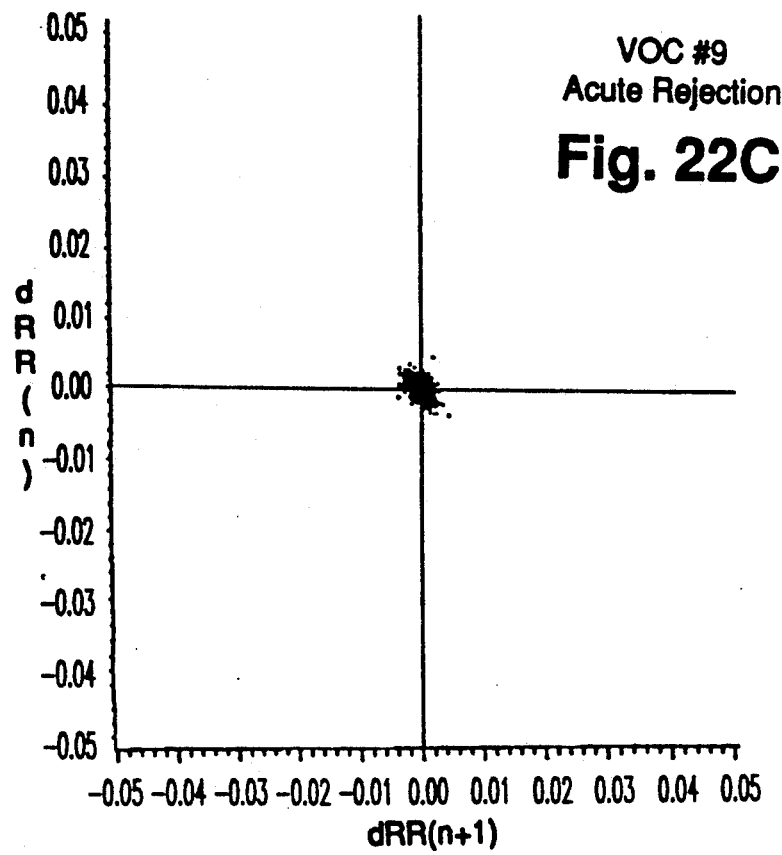
Figure 22D:
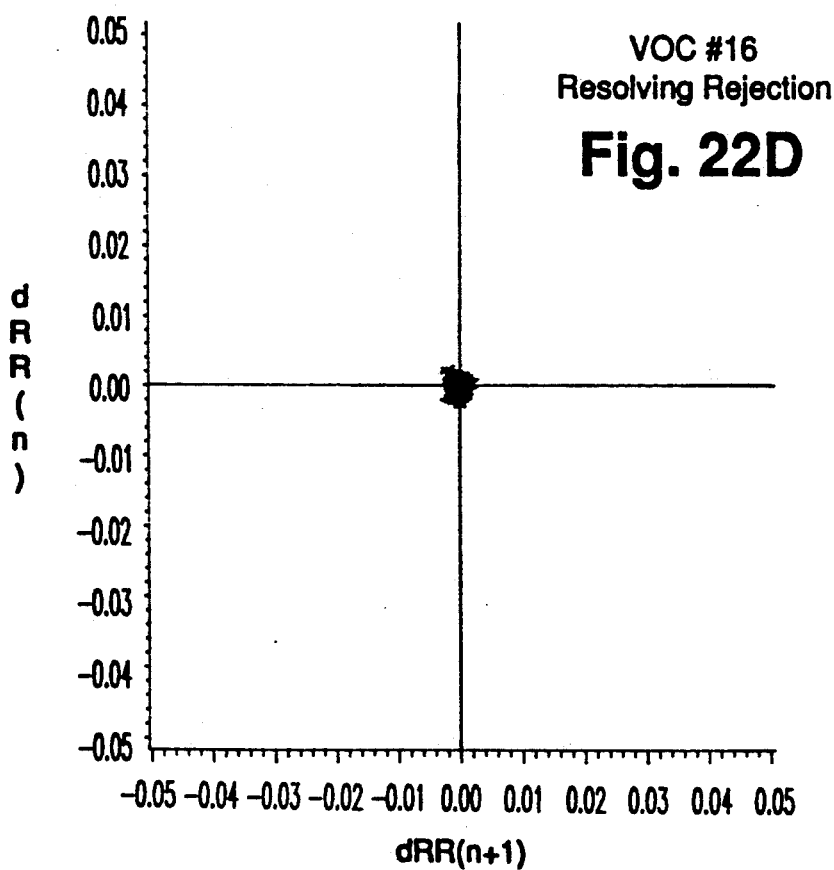

The methods described are able to detect repeated episodes of rejection. The DTI plot obtained for patient VOC four days after transplant (FIG. 22A) demonstrated collapse of points around the origin. EMBx revealed acute rejection. The patient was started on a three-day course of IV steroids. One day after receiving intravenous steroids (the fifth day after transplant) the points on the DTI plot had expanded (FIG. 22B) compared to the previous day's study. One week later (the 12th day after transplant), the patient complained of fatigue. Physical examination revealed low blood pressure, a sign of cardiac failure. An emergency biopsy showed severe acute rejection. Compared with the previous positive DTI plot, the points on this study were condensed even further around the origin, coinciding with a worsening of histologic diagnosis, as shown in FIG. 22C. This result suggests that the DTI plot may enable the clinician to grade the severity of rejection. More generally, the methods described herein may reflect the degree of cardiac dysfunction. In this case, the increase collapse of points around the origin corresponded with a marked deterioration in the patient's cardiac function. FIG. 22D shows ongoing rejection on the 16th day after transplant. The biopsy corresponding to this DTI plot showed resolving rejection, but it is believed that any resolution was minimal.

Patient VOC experienced one additional episode of rejection episodes, the latest being diagnosed 31 days after transplant. FIG. 22E shows the DTI plot for patient VOC two days after treatment for the third episode of rejection, and FIG. 22F for four days later, showing resolving rejection. In each case, the DTI plot enabled detection of the onset of, and recovery from, rejection. After treatment for patient VOC's latest rejection episode, the points on the DTI plot expanded greatly compared with the patient's first study. This represents his new baseline.

Patients have been studied as far as six months after transplant. Preliminary evidence suggests that patients develop a stable pattern of points over time. As described above, a change in the pattern of points suggests a change in cardiac dynamics. Months (and more often, years) after transplant, some transplant recipients undergo partial renervation of the heart. A renervated heart is far more responsive to stimuli such as fright, which causes a jump in adrenaline, than a denervated heart. At present, this condition is detected experimentally using intra-cardiac injections of tyramine, a substance related to adrenaline. In principle, DTI plots should detect this change in innervation non-invasively.

The graphical and analytical techniques described in this invention represent various methods for discerning critical changes in the dynamics of the transplanted heart. Successive interval, DTI, and recurrence plots uncover relationships between successive heart beats, and offer insight into the dynamics underlying cardiac rhythm. Both canine and human experiments have taught us to associate certain patterns with non-rejection, and other patterns with rejection. In general, plots for non-rejecting hearts show organized structures such as X- and leaf-shapes. A gap in the center of the attractor is present in most cases. Trajectories through these data sets appear smooth, suggesting a clear dependence of the current RR interval on the preceding interval.

In contrast, plots depicting rejection show tight clustering of points near the origin. This clustering suggests that the heart rate time series has become less complex, and therefore lower dimensional. Trajectories through these attractors appear jerky and random. The relationship between successive heart beats has become altered, perhaps even obliterated. It is likely that the figures for non-rejection and rejection presented in this application represent extremes of cardiac behavior in the face of rejection. Rejection is gradual process. With 24 hour monitoring, the invention will be able to witness the onset of, and recovery from rejection. This analysis may reveal transition states between non-rejection and rejection, and may establish even firmer grounds for arriving at a proper diagnosis.

Thus, as described above the invention provides an accurate, inexpensive, and patient-friendly noninvasive method and apparatus for diagnosis of heart rejection. Although the invention has been described in its preferred form, those of skill in the art will readily recognize that many changes and modifications may be made thereto without departing from the spirit and scope of the claims appended hereto.

Mutual Information Programs

EKBIN
```
/*
ekf.c  -- code to convert ascii floating point
numbers to binary floating point file for rapid reading;
*/
#include <stdio.h>
#define LIM 80
main(argc,argv)
int argc;
char **argv;
{
FILE *fi, *fo, *fopen();
int i,j,ret;
char s[LIM], *p;
float x;

if((fi = fopen(argv[1],"r")) == NULL){
        fprintf(stderr,"%s: can't open %s for input\n",
            argv[0],argv[1]);
        exit(1); }
    if((fo = fopen(argv[2],"w+")) == NULL){
        fprintf(stderr,"%s: can't open %s for output\n",
            argv[0],argv[2]);
        exit(1); }
    j = 0;
    p = s;
    x = 0.0;
    while((p = fgets(s,LIM,fi)) != NULL){
            if((ret=sscanf(s,"%f",&x)) != 1){
                fprintf(stderr,
                    "trouble converting item %d\n",j);
                exit(1); }
            if((ret = fwrite(&x,sizeof(float),1,fo)) != 1){
                fprintf(stderr,"%s: trouble writing %s \n",
                    argv[0],argv[2]);
                exit(1); }
            j++;
    }
    fclose(fi);
    fclose(fo);
}

INTERLEAV
/* interleave(n,d)
interleave combines d integer files which should have been created by scode
into a single file and rearranges the bits into a form used by polly (see
polly.c for details).
ex:   cat x y z|interleave 1024 3 >vect */
```

```c
#include <stdio.h>
main (argc, argv)
int     argc;
char    *argv[];
{
    int     n, n1, logn, w;
    unsigned int    *in, *out;
    register unsigned int   t1, t2;
    register int    k, i, j, d;
    n = atoi (argv[1]);         /* n is the number of vectors. n should be
            a power of 2 */
    d = atoi (argv[2]);         /* d is the number of coordinates in a
                    vector */
    n1 = 0;
    for (i = 1; n1 <= n; i++)
     n1 = 1 << i;
    logn = i - 2;
    n1 = 1 << logn;       /* n1 is the largest power of 2 <= n */
    w = (logn * d - 1) / 32 + 1;
    in = (unsigned int *) malloc (d * n * sizeof (unsigned int));
    for (i = 0; i < d; i++)    /* read in the components */
     for (j = 0; j < n; j++)
        in[j * d + i] = getw (stdin);
    out = (unsigned int *) malloc (w * sizeof (unsigned int));
    for (i = 0; i < n1; i++)   /* for every vector */
    {
     for (j = 0; j < logn; j++)
        {              /* for every bit position of the input */
        t2 = 0;
        for (k = 0; k < d; k++)
            {          /* for every component */
         t1 = in[i * d + k];
         in[i * d + k] = t1 >> 1;
         t2 <<= 1;
         t1 &= 1;   /* get an input bit */
         t2 |= t1;
         }
        for (k = w-1; k > 0; k--) /* paste d bits on the output */
            {              /* Thanks to Willem van de Water */
         t1 = out[k-1] >> (32 -d);
         out[k] = (out[k] << d) | t1;
         }
        out[0] = (out[0] << d) | t2;
        }
     (void) fwrite ((char *)out, sizeof (int), w, stdout);
     /* write the output    */
     }
}
POLLY
/*   polly(n,d)
calculates the total redundancy (generalized mutual information) of a
sample of n d dimensional vectors.
Ex: cat vect|polly 1024 3  where vect is a file of interleaved coded
vectors
n-   #of vectors (power of 2)
d-   #of degrees of freedom of vectors
*/
#include <stdio.h>
#include <math.h>
int  -  mask, d, ttd, flag;
double ci, logttd;
main (argc, argv)
int     argc;
char    *argv[];
{
    int     n, n1, i, logn, w, l, *in;
    double  log (), evlbx (), rks (), inf, rn;
    n = atoi (argv[1]);
```

```
    d = atoi (argv[2]);
    nl = 1;
    for (i = 1; nl <= n; i++)
     nl = 1 << i;
    logn = i - 2;           /* logn is the integer part of base 2 log
                               of n */
    nl = 1 << logn;
    ttd = 1 << d;           /* ttd is two to the d */
    mask = ttd - 1;         /* d least significant bits of mask are
                               set */
    ci = rks (ttd - 1);
    rn = (double) ttd;
    rn = (rn - 1) / rn;
    ci = rn * rn * ci;      /* ci is confidence interval for chi
                               square test */
    logttd = d * log (2.0);
    w = (logn * d - 1) / 32 + 1;/* w is the number of 32 bit words needed
                               to represent each event */
    l = n * w;              /* l is # of words to store all the events
                               */
    in = (int *) malloc (l * sizeof (int));
    if (in == NULL)
    {
     fprintf (stderr, "malloc fail in main\n");
     exit (0);
    }
    fread (in, sizeof (int), l, stdin);
    flag = 1;               /* force subdivision at first level of
                               evlbx */
    inf = evlbx (in, nl, logn * d);/* all the work is done here */
    rn = nl;
    inf = (inf / rn - log (rn));
    inf = inf / log (2.0);
    printf (" %5.2f ", inf);
}
double  evlbx (ix, n, b)
int     n, b;
unsigned int    *ix;
/*
    USE:        Redundancy = (evlbx()/n -log(n))/(d-1)

ARGUMENTS:
ix[]    The codes of the events in the element. Bits are preinterleaved,
and their order is inverted. starting with the least significant bit
position the representation of an event in a 3d calculation is...

bit#
    ix[0]  0    Most significant bit of component #0
           1    Most significant bit of component #1
           2    Most significant bit of component #2
           3    2nd most significant bit of comp #0
           4    2nd most sig bit of comp #1
           :
           :
           30   10th most sig bit of comp #0
           31   10th most sig bit of comp #1
    ix[1]  0    10th most sig bit of comp #2
           1    11th most sig bit of comp #0
    etc.
n       # of events in the element.
b       # of significant bits left in each event of ix EXTERNALS:
mask A mask with only d bits set, for stripping  off one level of ix
d    The dimension of the vectors being worked on.
ttd  2**d
ci   Confidence Interval. The 20% level for a chi-square
     test of ttd-1 degrees of freedom.
```

```
   logttd    log(ttd) or d*log(2)
   flag force subdivision on first level of recursion.
*/
{
   extern int   mask, d, ttd, flag;
   extern double  ci, logttd;
   int      w, bnew, i, j, k, l, wnew, *nd;
   unsigned int **dix;
   double  f, s, t, inf, log (), rks ();
   w = (b - 1) / 32 + 1;      /* #of words needed to hold b bits */
   bnew = b - d;              /* # of bits left after d used at this
                    level */
   wnew = (bnew - 1) / 32 + 1;   /* # of words needed at next level */
   nd = (int *) malloc (ttd * sizeof (int));
/* allocate array for event count of daughter elements */
   for (j = 0; j < ttd; j++) /* Now count events in daughter elts */
   nd[j] = 0;
   for (i = 0; i < n; i++)
   nd[ix[i * w] & mask]++;
   f = (double) n / (double) ttd;/* do test for sub-structure */
   s = 0.0;              /* details at end of this file */
   for (i = 0; i < ttd; i++)
   {
     t = (double) nd[i] - f;
     s += t * t;
   }
   s = s / n;
   if ((s > ci) || (flag == 1))

{               /* If substructure found then subdivide the
current partition element */
      flag = 0;      /* don't force subdivision after the first level */
      dix = (unsigned int **) malloc (ttd * sizeof (int *));
      for (j = 0; j < ttd; j++)
      {
         if (nd[j] > 1)   /* allocate arrays for events in daughter
                  elts */
           dix[j] = (unsigned int *) malloc (nd[j] * wnew * sizeof (int));
         else
           dix[j] = NULL;
         nd[j] = 0;
      }

/* divide events in ix into appropriate daughter elts and discard the
      d bits that have been used up */
      for (i = 0; i < n; i++)
      {
          k = ix[i * w] & mask;
          if (dix[k] != NULL)
          {
           for (l = 0; l < wnew; l++)
           {
              dix[k][nd[k] * wnew + l] = ix[i * w + l] >> d;
              dix[k][nd[k] * wnew + l] |= ix[i * w + l + 1] << (32 - d);
           }
          }
          nd[k]++;
      }
     free (ix);
   /* Invoke recursion formula 20b from Fraser & Swinney Phys Rev A Feb.
      86 */
     inf = (double) n * logttd;
     for (j = 0; j < ttd; j++)
     {
         if (nd[j] > 1)
         {
           inf += evlbx (dix[j], nd[j], bnew);
         }
```

```
        }
      free (dix);
      }
      else              /* when no substructure was found */
      {
       free (ix);
       s = (double) n;
       inf = s * log (s);  /* PRA 2/86 Eqn# 20a */
      }
      free (nd);
      return inf;
}
double  rks (n)
int     n;
{
    double  r, rn, sqrt ();
/* returns the 20% confidence interval of the chi-square test for n
degrees of freedom
*/
    if (n == 3)
      return 1.547;
    if (n == 7)
      return 1.400;
    if (n == 15)
      return 1.287;
    if (n == 31)
      return 1.205;
    rn = n;
    r = 1.0 + 1.1314 / sqrt (rn) -.24 / rn;
    return r;
}
/* chi square test.
      m-    # of boxes
      ni-   # of elements in the ith box
      N-    sum of ni
      var-  variance of the assumed parent distribution
      rks-  reduced chi-square statistic
      ssq-  sample variance
      Hypothesis A;  The parent distribution is a flat multinomial
(see Drake page 275).
      The chi-square test consists of rejecting A if the probability of
getting a {ni} more nonuniform than the one measured is less than .2.
      (see Bevington pg 188 & 315)
      rks = ssq/var                              188 Bevington
      ssq = (sum (ni - E(ni))**2)/(m - 1)        everyone knows
      var = N(1/m)(1 - 1/m) = N*(m - 1)/m**2     Drake pg 275
      rks = (sum(ni - N/m)**2) /( ((m-1)/m)**2 *N)
      The 20% points of rks are in Bevington pg 315.
      Also see Knuth "Seminumerical Algorithms" page 39
      */
JL2
#include <stdio.h>
#define LEN 4096
main(argc,argv)
int argc;
char **argv;
{
int Td[8], i,j,k;
for(j=0;j<100;j++){
Td[2] = 0;
Td[1] = j * 8 + 1;
for(i=1;i<3;i++){
printf("cat %s|tail +%dc|scode %d >>/tmp/redun.a \n",argv[1],Td[i],LEN);
} /* 2-D loop */
printf("echo %d 'cat /tmp/redun.a|interleave %d 2 |polly %d 2'
\n",j,LEN,LEN);
printf("rm /tmp/redun* \n");
} /* end j */
}
```

SCODE

```c
/* scode.c(length)
use: cat rosx|scode 16384 >temp
This program takes floats in machine rep from stdin and produces ints in
machine rep on stdout. The order of the output is the same as the order of
the input. The program access arrays in random order, so for files to big
to sit in memory the program takes a very long time to finish.
*/
#include <stdio.h>
main (argc, argv)
int     argc;
char    *argv[];
{
    int     *in, *out, i, i1, i2, j, n,
            *outlm, *inlam, *inlbm, *inla, *inlb, *outl;
    float   *r;
    n = atoi (argv[1]);
    r = (float *) malloc (n * sizeof (float));
    in = (int *) malloc (n * sizeof (int));
    out = (int *) malloc (n * sizeof (int));
    for (i = 0; i < n; i++)
      in[i] = i;
    fread (r, sizeof (float), n, stdin);
 /* sort indices according to the size of the input floats */
    for (i1 = 1; i1 < n; i1 <<= 1)
    {
        i2 = i1 << 1;
        /*  i1 is length of sorted sub-arrays i2 is length of array to be
produced   */
        for (j = 0; j < n; j += i2)
        {
            inla = &in[j];
            inlam = inlb = &in[j + i1];
            inlbm = &in[j + i2];
            outl = &out[j];
            outlm = &out[j + i2];
            while (outl < outlm)
            {
              if (inla >= inlam)
                  while (outl < outlm)
                      *outl++ = *inlb++;
              else
                  if (inlb >= inlbm)
                      while (outl < outlm)
                          *outl++ = *inla++;
                  else
                    if (r[*inla] < r[*inlb])
                        *outl++ = *inla++;
                    else
                        *outl++ = *inlb++;
            }
        }
        outl = in;
        in = out;
        out = outl;
    }
/*  having finished the sort, invert the array in[]   */
    for (i = 0; i < n; i++)
      out[in[i]] = i;
/*  write the result out    */
    fwrite (out, sizeof (int), n, stdout);
}
```

What is claimed is:

1. A method for diagnosing heart rejection in a mammal with a transplanted heart, wherein the time interval between heart beats is an interbeat interval, and a series of interbeat intervals has an associated pattern, comprising the steps of:
   (a) measuring the interbeat intervals in the transplanted heart and obtaining a pattern associated with its intervals; and
   (b) diagnosing heart rejection based on the pattern of interbeat intervals using nonlinear dynamical systems analysis.

2. A method for diagnosing and treating heart rejection in a manual with a transplanted heart, wherein the time interval between heart beats is an interbeat interval, and a series of interbeat intervals has an associated pattern, comprising the steps of:
   (a) measuring the interbeat intervals in the transplanted heart and obtaining a pattern associated with the intervals; and
   (b) diagnosing heart rejection based on the pattern of interbeat intervals using nonlinear dynamical systems analysis; and
   (c) administering pharmaceutical agents to control rejection based on the diagnosis made in step (b).

3. A method for diagnosing heart rejection in a mammal with a transplanted heart wherein the time interval between heart beats is an interbeat interval, and a series of interbeat intervals has an associated pattern, comprising the steps of:
   (a) measuring the interbeat intervals in the transplanted heart shortly after the heart is transplanted to establish a baseline reference for future comparison to provide a baseline measurement;
   (b) measuring the interbeat intervals in the transplanted heart and obtaining a pattern associated with the intervals at a point later in time than the baseline measurement to provide a later measurement; and
   (c) diagnosing heart rejection based on comparing the pattern of interbeat intervals of the later measurement to the baseline measurement using nonlinear dynamical systems analysis.

4. A method for diagnosing and treating heart rejection in a mammal with a transplanted heart, wherein the time interval between heart beats is an interbeat interval, and a series of interbeat intervals has an associated pattern comprising the steps of:
   (a) measuring the interbeat intervals in the transplanted heart shortly after the heart is transplanted to establish a baseline reference for future comparison to provide a baseline measurement;
   (b) measuring the interbeat intervals in the transplanted heart and obtaining a pattern associated with the intervals at a point later in time than the baseline measurement to provide a later measurement;
   (c) diagnosing heart rejection based on comparing the pattern of interbeat intervals of the later measurement to the baseline measurement using nonlinear dynamical systems analysis; and
   (d) administering pharmaceutical agents to control rejection based on the diagnosis made in step (c).

5. The method according to claim 1, 2, 3 or 4 wherein the interbeat intervals are measured with a precision equal to or greater than 1 millisecond resolution.

6. The method of claim 1, 2, 3, 4 or 5 wherein the step of diagnosing heart rejection includes using a differential time interval plot to reveal the pattern of interbeat intervals.

7. The method of claim 1, 2, 3, 4 or 5 wherein the step of diagnosing heart rejection includes using a recurrence plot to reveal the pattern of interbeat intervals.

8. The method of claim 1, 2, 3, 4 or 5 wherein the steps of diagnosing heart rejection includes using a method of delays to create a data set for plotting to reveal the pattern of interbeat intervals.

9. The method according to claim 3 or 4 wherein the pattern from the later obtained measurements are compared to the baseline measurements using automated software driven pattern analysis.

10. The method according to claim 3 or 4 wherein the pattern from the later obtained measurements are compared to the baseline measurements using weighted values obtained from a neural network trained to recognize changes in patterns associated with rejection.

11. Apparatus for diagnosing heart rejection in a mammal with a transplanted heart, wherein the time interval between heart heats is an interbeat interval, and a series of interbeat intervals has an associated pattern, comprising:
   an amplifier for amplifying an EKG signal from leads attached to the chest of the mammal;
   a level detector receiving the amplified EKG and set to detect a component of the QRS complex of the EKG to produce a signal indicating the occurrence of a heart beat, whereby the detector produces a series of signals corresponding to the occurrence of heart beats;
   a timer means for responsive to said series of signals for timing the intervals between heart beats to produce a series of interbeat interval measurements;
   means for obtaining a pattern of interbeat interval measurements;
   means for analyzing the pattern of interbeat interval measurements using nonlinear dynamical systems analysis for an indication of rejection; and
   an indicator for indicating to a user of the apparatus whether or not rejection has been detected by the means for analyzing.

12. The apparatus of claim 11 wherein said timer has a precision of 1 millisecond or greater.

13. The apparatus of claim 11 wherein the level detector is an electronic trigger, and the signal is a pulse.

14. Apparatus for diagnosing heart rejection in a manual with a transplanted heart, wherein the time interval between heart beats is an interbeat interval, and a series of interbeat intervals has an associated pattern, comprising:
   an amplifier for amplifying an EKG signal from leads attached to the chest of the mammal;
   means for timing the intervals between heart beats and producing a series of interbeat interval measurements;
   means for obtaining a pattern of interbeat interval measurements; and
   means for analyzing the pattern of interbeat interval measurements using nonlinear dynamical systems analysis for an indication of rejection;
   an indicator for indicating to a user of the apparatus whether or not rejection has been detected by the means for analyzing.

15. The apparatus of claim 14 wherein said timing means has a precision of 1 millisecond or greater.

16. A method of ambulatory monitoring for an ambulatory mammal, comprising the steps of:
(1) providing a monitoring apparatus comprising
   (a) an amplifier for amplifying an EKG signal from leads adapted for attachment to the chest of the mammal;
   (b) a level detector receiving the amplified EKG and set to detect the R wave upstroke of the QRS complex of the EKG to produce a signal indicating the occurrence of the upstroke, whereby the detector produces a series of signals corresponding to the occurrence of R waves;
   (c) a timer responsive to said series of signals for timing the intervals between R waves to produce a series of RR interval measurements in digital form;
   (d) an analog to digital converter for sampling the analog EKG to produce a digitized EKG;
   (e) a storage device for storing the series of RR interval measurements and the digitized EKG; and
   (f) a battery for supplying power to the amplifier, level detector, timer, analog to digital converter and storage device;
(2) attaching the monitoring apparatus and said leads to the ambulatory mammal for a period of time and storing a series of RR interval measurements obtained from the mammal's EKG signal, said RR interval measurements being stored in said storage device, and obtaining a pattern associated with the interval measurements; and
(3) diagnosing heart rejection based on an analysis of the pattern of RR interval measurements stored in said storage device using nonlinear dynamical systems analysis.

17. A method for diagnosing heart rejection in a mammal with a transplanted heart comprising the steps of:
   (a) measuring the interbeat intervals in the transplanted heart shortly after the heart is transplanted to establish a baseline reference for future comparison;
   (b) measuring the interbeat intervals in the transplanted heart at a point later in time than the baseline measurement, and obtaining a pattern associated with the intervals and diagnosing heart rejection based on comparing the pattern of interbeat intervals of the later measurement to the baseline measurement wherein the pattern from the later obtained measurements are compared to the baseline measurements using weighted values obtained from a neural network trained to recognize changes in patterns associated with rejection.

18. A method for diagnosing and treating heart rejection in a mammal with a transplanted heart, comprising the steps of:
   (a) measuring the interbeat intervals in the transplanted heart shortly after the heart is transplanted to establish a baseline reference for future comparison;
   (b) measuring the interbeat intervals in the transplanted heart at a point later in time than the baseline measurement and obtaining a pattern associated with the intervals;
   (c) diagnosing heart rejection based on comparing the pattern of interbeat intervals of the later measurement to the baseline measurement, wherein the pattern from the later obtained measurements are compared to the baseline measurements using weighted values obtained from a neural network trained to recognize changes in patterns associated with rejection.; and
   (d) administering pharmaceutical agents to control rejection based on the diagnosis made in step (c).

* * * * *

UNITED STATES PATENT AND TRADEMARK OFFICE
CERTIFICATE OF CORRECTION

PATENT NO. : 5,285,793
DATED : February 15, 1994
INVENTOR(S) : Slovut et al.

It is certified that error appears in the above-indentified patent and that said Letters Patent is hereby corrected as shown below:

In column 33, line 9 please delete "its" and insert --the--

In column 33, line 14 please delete "manual" and insert --mammal--

In column 34, line 50 please delete "manual" and insert --mammal--

Signed and Sealed this

Fifth Day of August, 1997

Attest:

Attesting Officer

BRUCE LEHMAN

*Commissioner of Patents and Trademarks*